(12) United States Patent
Leshno

(10) Patent No.: US 11,911,018 B2
(45) Date of Patent: Feb. 27, 2024

(54) OCULAR SURGICAL INSTRUMENT

(71) Applicant: TEL HASHOMER MEDICAL RESEARCH, INFRASTRUCTURE AND SERVICES LTD., Ramat Gan (IL)

(72) Inventor: Ari Leshno, Tel Aviv (IL)

(73) Assignee: TEL HASHOMER MEDICAL RESEARCH, INFRASTRUCTURE AND SERVICES LTD., Ramat Gan (IL)

( * ) Notice: Subject to any disclaimer, the term of this patent is extended or adjusted under 35 U.S.C. 154(b) by 495 days.

(21) Appl. No.: 17/271,189

(22) PCT Filed: Aug. 29, 2019

(86) PCT No.: PCT/IL2019/050970
§ 371 (c)(1),
(2) Date: Feb. 24, 2021

(87) PCT Pub. No.: WO2020/044347
PCT Pub. Date: Mar. 5, 2020

(65) Prior Publication Data
US 2021/0186478 A1 Jun. 24, 2021

Related U.S. Application Data

(60) Provisional application No. 62/724,098, filed on Aug. 29, 2018.

(51) Int. Cl.
*A61B 17/02* (2006.01)
*A61B 90/00* (2016.01)
*A61B 17/00* (2006.01)

(52) U.S. Cl.
CPC .... *A61B 17/0231* (2013.01); *A61B 17/00491* (2013.01); *A61B 90/06* (2016.02);
(Continued)

(58) Field of Classification Search
CPC ..... A61B 17/0231; A61B 90/06; A61B 90/08; A61B 17/00491; A61B 2090/061; A61B 2090/0807; A61B 2017/00858
See application file for complete search history.

(56) References Cited

U.S. PATENT DOCUMENTS 5,797,932 A 8/1998 Min et al.
6,626,922 B1 * 9/2003 Hart ................ A61B 17/02
606/157

(Continued)

FOREIGN PATENT DOCUMENTS

BE 1017064 A6 1/2008
CN 2262415 Y 9/1997

(Continued)

OTHER PUBLICATIONS

PCT Search Report for International Application No. PCT/IL2019/050970; dated Dec. 31, 2019; 4 pp.

(Continued)

*Primary Examiner* — Zade Coley
(74) *Attorney, Agent, or Firm* — The Roy Gross Law Firm, LLC; Roy Gross

(57) ABSTRACT

Apparatus for performing an ocular surgery, the apparatus comprising: a support housing having a bottom configured to be positioned on the sclera of an eye during performance of an ocular surgery; a muscle hook holder connected to the support housing and configured to hold an ocular muscle hook so that the ocular muscle hook is translatable to elevate an ocular muscle away from the eye during performance of the surgery; and a set of graduation markings on the support housing useable to determine a distance that the ocular muscle hook is translated to elevate the ocular muscle.

16 Claims, 18 Drawing Sheets

(52) U.S. Cl.
CPC .... *A61B 90/08* (2016.02); *A61B 2017/00858* (2013.01); *A61B 2090/061* (2016.02); *A61B 2090/0807* (2016.02)

(56) References Cited

U.S. PATENT DOCUMENTS

| | | | | |
|---|---|---|---|---|
| 6,761,724 B1 * | 7/2004 | Zrenner | ................. | A61F 9/007 606/166 |
| 2009/0177138 A1 * | 7/2009 | Brown | ................ | A61F 9/00781 606/108 |
| 2017/0319382 A1 | 11/2017 | Moon et al. | | |

FOREIGN PATENT DOCUMENTS

| | | | | | |
|---|---|---|---|---|---|
| CN | 201324318 | Y | | 10/2009 | |
| CN | 203107409 | U | | 8/2013 | |
| CN | 203425105 | U | | 2/2014 | |
| CN | 107080617 | A | | 8/2017 | |
| GB | 2335601 | A | | 9/1999 | |
| GB | 2369056 | A | * | 5/2002 | ............. A61B 17/02 |
| JP | 2001517486 | A | | 10/2001 | |
| JP | 2016171911 | A | | 9/2016 | |
| JP | 2016536055 | A | | 11/2016 | |
| WO | 2014073049 | A1 | | 5/2014 | |
| WO | 2015054075 | A1 | | 4/2015 | |

OTHER PUBLICATIONS

PCT Search Report for International Application No. PCT/IL2019/050970; dated Dec. 31, 2019; 5 pp.
PCT Search Report for International Application No. PCT/IL2019/050970; dated Mar. 2, 2021 ; 6 pp.

* cited by examiner

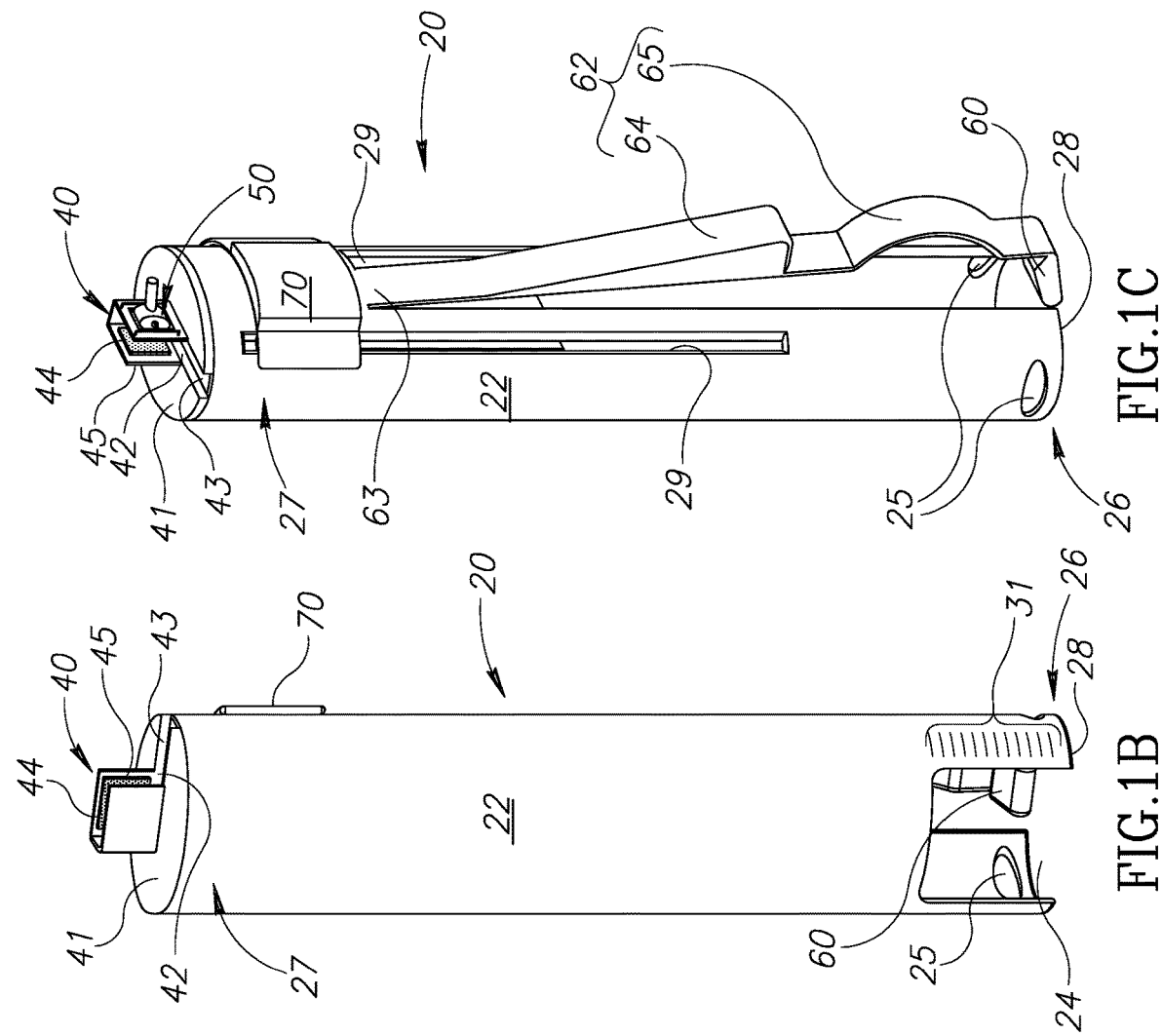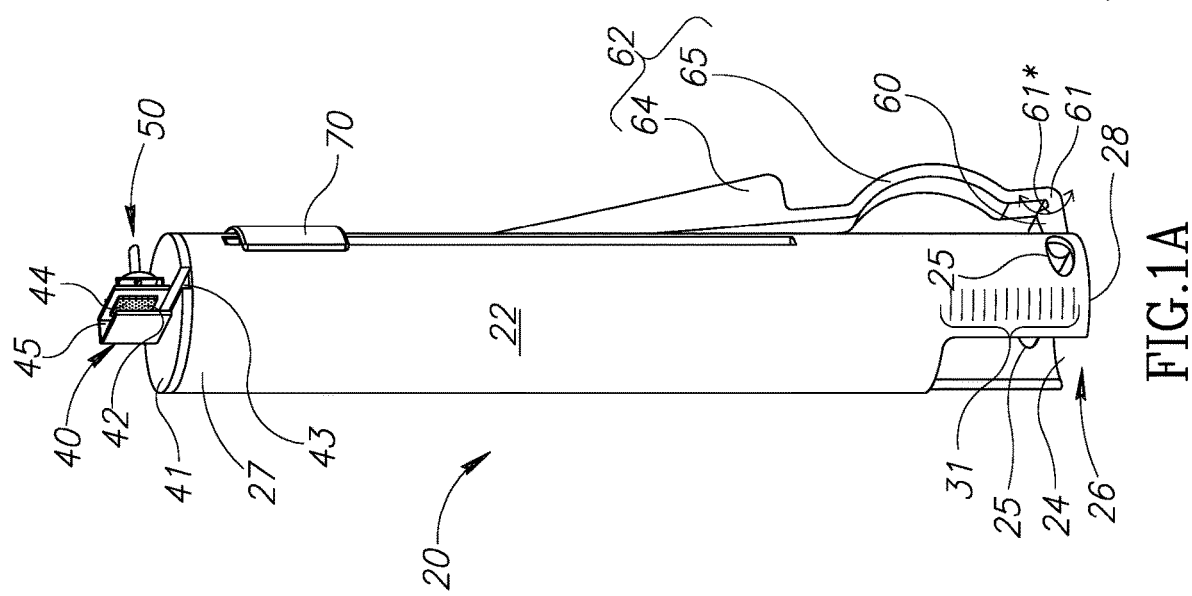

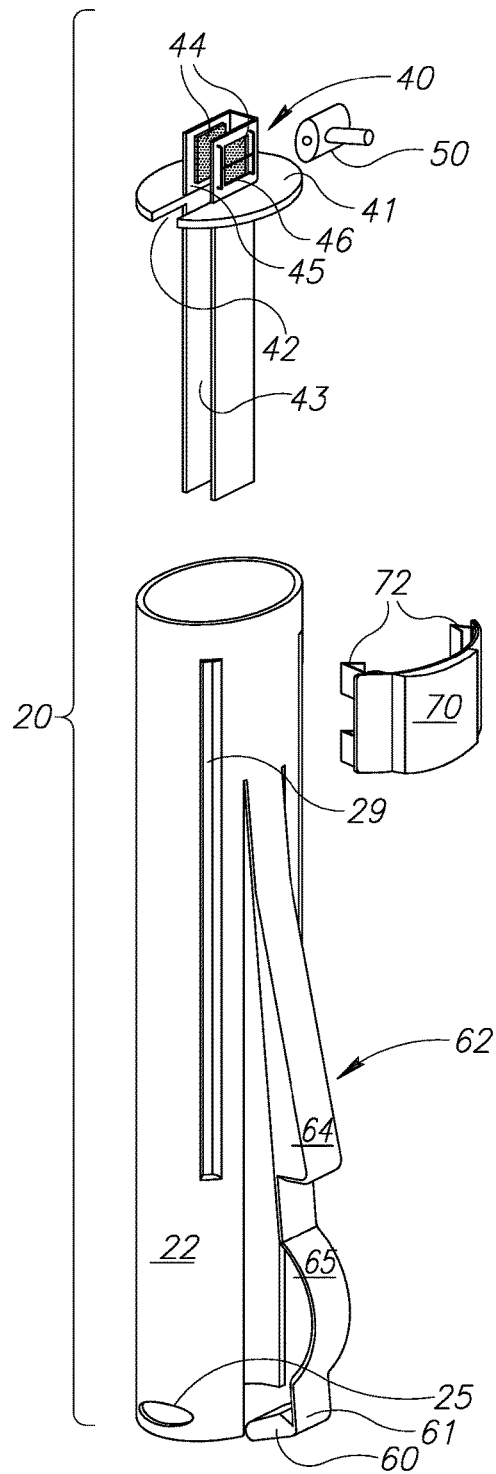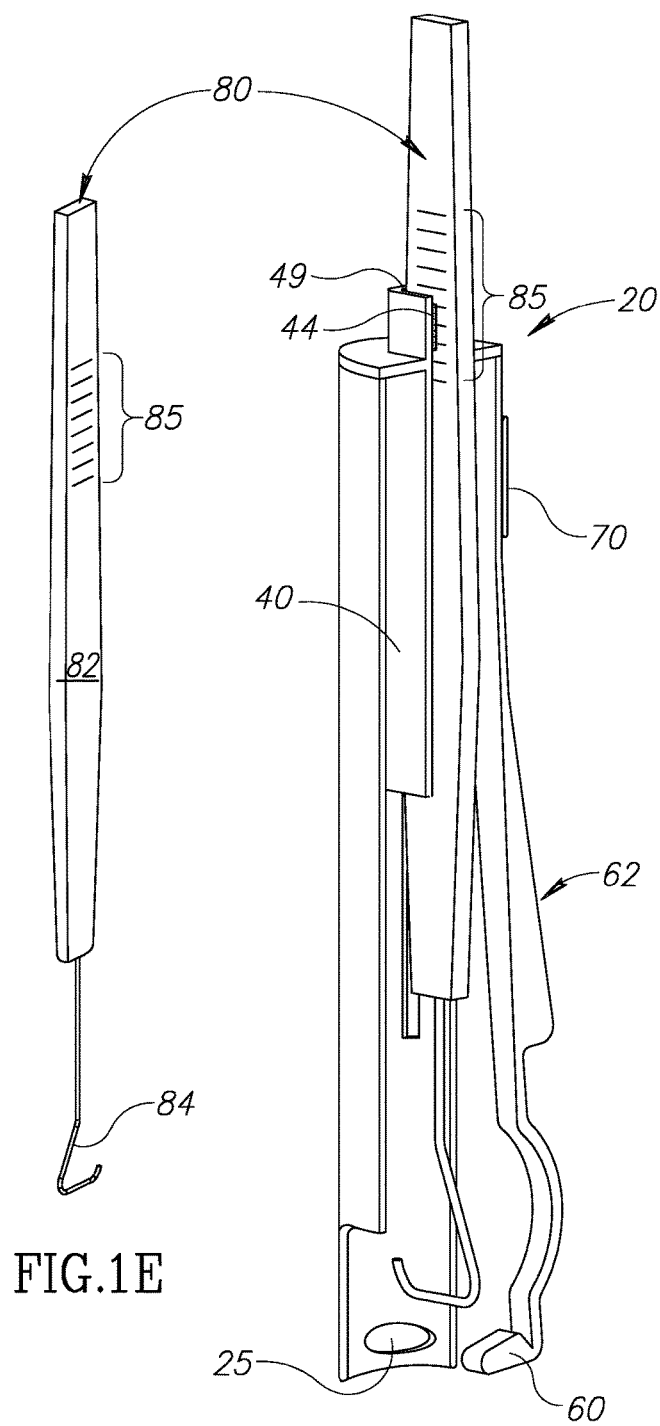
FIG.1D  FIG.1E  FIG.1F

OCULAR SURGICAL INSTRUMENT

RELATED APPLICATIONS

The present application is a National Phase of PCT Patent Application No. PCT/IL2019/050970 having International filing date of Aug. 29, 2019, which claims the benefit under 35 U.S.C. 119(e) of U.S. Provisional Application 62/724,098 filed on Aug. 29, 2018, the disclosure of which are all incorporated herein by reference.

FIELD

Embodiments of the invention relate to an apparatus for performing ocular surgery.

BACKGROUND

"Crossed-eyes" formally referred to by the medical profession as "strabismus" is a condition in which gaze directions of both of a person's eyes do not simultaneously align to a same point of regard. Gaze direction of a person's eye is controlled by six ocular muscles, referred to as extraocular muscles, that extend from a fibrous ring at the back of the eye orbit to respective attachment regions on the sclera the eye. The ocular muscles include four recti muscle (superior, inferior, lateral and medial) and two oblique muscles (inferior and superior).

Strabismus may be surgically corrected by strengthening or weakening of one or more extra ocular muscles to realign both eye in primary gaze position. In order to strengthen a muscle a procedure referred to as a resection procedure is usually performed, which involves excising a portion of the muscle near an attachment region of the muscle to the sclera of the eyeball and reattaching the muscle shortened by the excision to or near to the original "native" attachment region. Conversely in order to weaken the muscle, a procedure referred to as a recession procedure is performed, in which the muscle is detached from its native attachment region on the sclera then reattached at a new attachment region located behind the native attachment region and closer to the fibrous ring at the back of the eye's orbit.

Spatial accuracy in excising a portion of an ocular muscle and in reattaching an ocular muscle is advantageously performed to tolerances of less than or equal to about a millimeter or two. Surgical correction of strabismus is a relatively complex procedure that typically requires the hands of a qualified surgeon, and due to the technical difficulties involved in in the procedure the hands of a skilled assistant to help retract and constrain the positions of the muscle and the eye so that the surgeon may operate safely.

SUMMARY

An aspect of an embodiment of the disclosure relates to providing a strabismus ocular surgical instrument, optionally referred to by the acronym "OSIN", for performing surgery on an ocular muscle that aids in efficiency and accuracy of performing strabismus surgery. In an embodiment OSIN comprises a support housing configured to be placed on an eye during eye surgery to correct strabismus and to hold an ocular muscle hook that is used during strabismus surgery to lift an ocular muscle of the eye away from the surface of the eyeball so that the muscle can be operated on. For holding the ocular muscle hook, OSIN may comprise a muscle hook holder and lock that enables the ocular muscle hook after being manipulated to engage the ocular muscle to be translated substantially along an axis of the hook to elevate the muscle by a desired distance from the eyeball and thereafter lock the ocular muscle hook in place to maintain the muscle elevated by the desired distance. In an embodiment the housing and/or the ocular muscle hook comprises graduation markings that may be used to determine a distance by which the ocular muscle hook is translated and the muscle displaced. The support housing is formed having at least one open access aperture through which a surgeon can introduce and operate a tool, such as a scalpel or surgical needle, to perform a step of a strabismus resection or recession procedure.

In an embodiment to facilitate reattachment of an elevated ocular muscle in a resection or recession procedure by gluing a region of the muscle to a desired reattachment location on the sclera, the housing comprises a clamping foot configured to be used to clamp the region of the elevated muscle to the reattachment location on the sclera for a setting period of the glue. Optionally, the housing comprises a foot stop against which the clamping foot can be pressed when clamping the region of the muscle to the reattachment location on the sclera. In an embodiment the clamping foot is formed at an end of a shank, which is attached to the housing and can be rotated to position the clamping foot to contact and clamp the muscle region to the desired reattachment location on the sclera.

In the discussion and claims, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment in an application for which the embodiment is intended. The word "or" is considered to be the inclusive "or" rather than the exclusive or, and indicates at least one of, or any combination of more than one of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

FIGS. 1A-1C schematically show perspective views from different vantage points of a OSIN for use having a clamping foot and configured to reinsert an ocular muscle by gluing in a strabismus surgery, in accordance with an embodiment of the disclosure;

FIG. 1D schematically shows an exploded view of the OSIN shown in FIGS. 1A-1C that shows detail of a muscle hook holder and lock, in accordance with an embodiment of the disclosure;

FIG. 1E schematically shows an ocular muscle hook, in accordance with an embodiment of the disclosure;

FIG. 1F schematically shows a cutaway view of the OSIN shown in FIGS. 1A-1D with the ocular muscle hook shown in FIG. 1E mounted to the OSIN, in accordance with an embodiment of the disclosure;

DETAILED DESCRIPTION

In the detailed description below construction and features of an OSIN having a clamping foot in accordance with an embodiment of the disclosure are described with reference to FIGS. 1A-1H. A resection procedure of a superior rectus muscle using the OSIN shown in FIGS. 1A-H is illustrated and discussed with reference to FIGS. 2A-2F. A variation of an OSIN having in addition to a clamping foot a foot stop is discussed with reference to FIG. 3A. A variation of an OSIN in which a clamping foot is configured to facilitate stapling an ocular muscle to reattach the muscle to an eye is discussed with reference to FIG. 3B. Discussion of an OSIN configured for performing a strabismus operation in which an ocular muscle is reattached by suturing is shown and discussed with reference to FIGS. 4A-4C. FIGS. 4D-4H illustrate a strabismus operation using the OSIN shown in FIGS. 4A-4C, and references to the figures are made in a discussion of the operation. FIGS. 5A and 5B show optional accessories to an OSIN for use in a strabismus operation in which a rectus muscle is reattached to an eye by suturing. Another variation of an OSIN and use of the variation are shown and discussed with reference to FIGS. 6A and 6B.

Figure 1G:
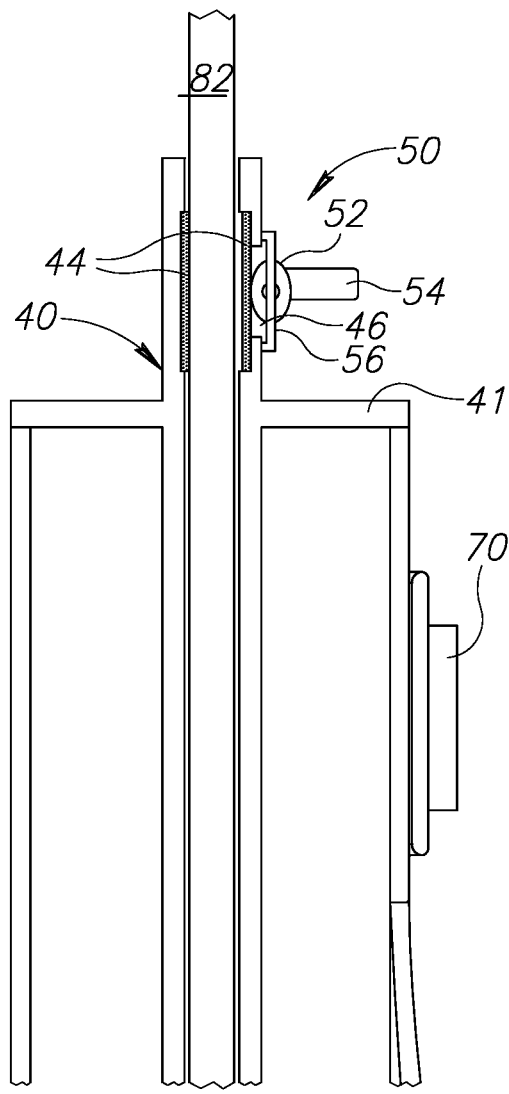
FIGS. 1G and 1H schematically shows operation of a muscle hook holder and lock similar to the muscle hook holder and lock shown in FIG. 1D, in accordance with an embodiment of the disclosure.

FIGS. 1A-1C schematically show different perspective views of an OSIN 20 operable to hold an ocular muscle hook for lifting an ocular muscle away from an eye during a strabismus operation, and to aid in reattaching the ocular muscle by gluing, in accordance with an embodiment of the disclosure. FIG. 1D schematically shows an exploded view of OSIN 20 that illustrates details of the construction of OSIN 20, in accordance with an embodiment of the disclosure that are not shown in FIGS. 1A-1C. FIG. 1E schematically shows an ocular muscle hook in accordance with an embodiment of the disclosure, and FIG. 1F schematically shows a perspective cutaway of OSIN 20 holding the ocular muscle hook shown in FIG. 1E. Not all features of OSIN 20 are labeled or shown in all of FIGS. 1A-1H. Figures of FIGS. 1A-1H in which a feature of OSIN 20 is best exhibited may be referenced for attention in the discussion below where the feature is discussed.

In an embodiment, OSIN 20 (FIGS. 1A-1C) comprises a tube-shaped support housing 22 optionally characterized by a substantially elliptical cross-section and formed having an access aperture 24 and glue injection ports 25 at a bottom end 26 of the housing, and a muscle hook holder 40 and lock 50 at a top end 27 of the housing. A bottom edge 28 of OSIN 20 may be formed to have a curvature matched to curvature of an eyeball of an eye for which OSIN is to be used to perform an operation and on which the bottom edge is placed during the operation. A set 31 of graduation markings that may be used to determine a distance by which an ocular muscle hook held by OSIN 20 is translated to elevate an ocular muscle during a strabismus operation may be located at bottom end 26 and extend in a direction towards top end 27 from a location near bottom edge 28. Optionally, adjacent graduation markings are spaced apart by equal distances. Bottom edge 28 may be covered with a layer (not shown) of a suitable biocompatible soft elastomer to prevent damage to the eye on which the bottom edge is placed.

OSIN 20 comprises a clamping foot 60 at an end of a shank 62 optionally connected to support housing 22 at a junction 63 (FIG. 1C) and integrally formed with support housing 22 to elastically splay outward from the housing. Clamping foot 60 may be connected to shank 62 by a relatively thin junction 61 that functions as a hinge to allow rotation of clamping foot 60 in directions indicated by arrow-head arc 61* shown in FIG. 1A. Shank 62 optionally comprises a ramp 64 and an arched segment 65. A shank slider 70 may be mounted to housing 20 by snap clips 72 shown in the exploded view of OSIN 20 in FIG. 1D that snap into slide slots 29 formed in the housing. Shank slider 70 is manually movable along slide slots 29 (FIGS. 1C, 1D) from a position near top end 27 of housing 20 in a direction towards bottom end 26 of housing 22 to press on ramp 64 of shank 62 and force the ramp and thereby the shank to rotate toward access aperture 24. Arched segment 65 may be configured to provide added bendability to the shank and clearance room to prevent interference with an ocular muscle hook held by muscle hook holder 40 when the hook is raised and the shank rotated towards the access aperture 24.

Muscle hook holder 40, shown in greater detail in FIG. 1D may protrude from a cap plate 41 that closes top end 27 of housing 22. The muscle hook holder is optionally formed to have a u-shaped cross-section and an open side 42, and the cap plate is optionally formed to have a slot 43. Open side 42 and slot 43 facilitate introducing an ocular muscle hook into OSIN 20, removing the ocular muscle hook from OSIN, and manipulating the ocular muscle hook during an operation when the ocular muscle hook is held by muscle hook holder 40. Muscle hook holder 40 may have at least one friction pad 44 mounted on an internal surface 45 of the holder. The at least one friction pad, which may be advantageously formed from a resilient elastomer, is configured to press snugly onto and hold a handle of an ocular muscle hook inserted into the holder, and operates to prevent free, unwanted motion of the ocular muscle hook. Optionally, muscle hook holder 40 comprises a pair of friction pads 44 on opposite regions of internal surface 45 of the muscle hook holder. The pair of friction pads may press onto a handle of an ocular muscle hook mounted in the muscle hook holder to sandwich and hold the handle between them.

Figure 1H:
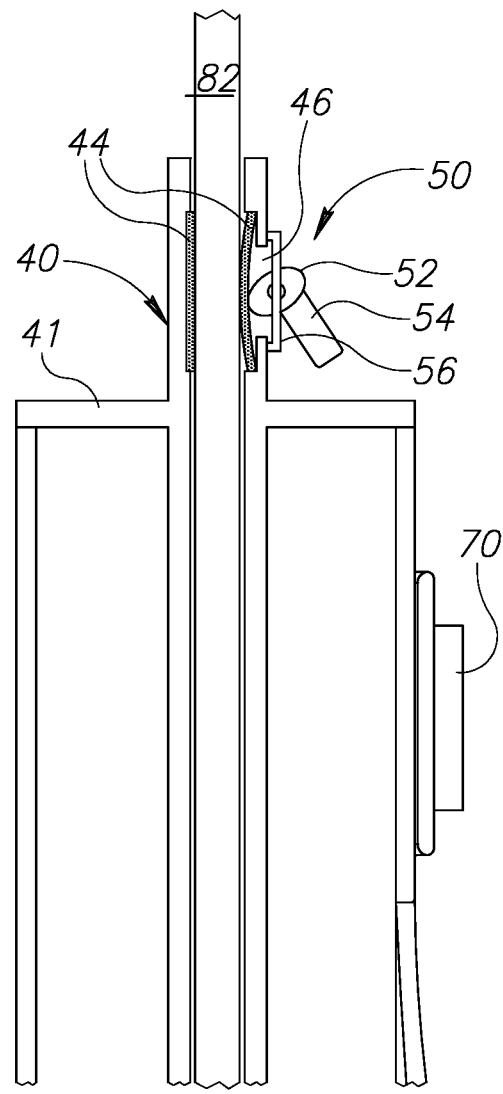

In the perspective of FIGS. 1A-1C only a single friction pad 44 of a pair of friction pads is seen. FIG. 1D, and FIGS. 1G and 1H discussed below, schematically show both friction pads 44 of a pair of friction pads that muscle hook holder 40 may comprise. FIG. 1E schematically shows an ocular muscle hook 80 having a handle 82 and a hook 84, and FIG. 1F schematically shows a perspective cutaway of OSIN 20 in which the ocular muscle hook shown in FIG. 1E is mounted in OSIN and at least one friction pad 44 presses on handle 82 of the ocular muscle hook.

Optionally, handle 82 of ocular muscle hook 80 comprises a set of graduation markings 85. When mounted in muscle hook holder 40 as shown in FIG. 1E, the graduation markings may be referenced to an edge 49 of muscle hook holder 40 to determine a distance by which ocular muscle hook 80 is translated to elevate an ocular muscle during a strabismus operation.

Lock 50 mounted to muscle hook holder 40 optionally comprises an elliptical or an eccentric circular locking wheel 52 that protrudes through a lock aperture 46 in the muscle hook holder to contact a friction pad 44 comprised in the muscle hook holder. The locking wheel, which by way of example is shown as an elliptical locking wheel, may be rotated to increase pressure on the friction pad that the locking wheel contacts and thereby pressure with which friction pads 44 holds the handle of the ocular muscle hook. Locking wheel 52 may be mounted to muscle hook holder 40 by any of various configurations of brackets for example, U-brackets 56 shown in FIGS. 1G and 1H. Optionally, lock 50 has a handle 54 for rotating locking wheel 52 and operating the lock.

FIGS. 1G and 1H schematically show cross-section views of lock 50 in open and closed positions respectively. Lock 50 has by way of example an elliptical locking wheel 52 and is mounted to muscle hook holder 40 by U-brackets 56. In the figures muscle hook holder 40 is holding handle 82 of ocular muscle hook 80 (FIG. 1E). In the open position shown in FIG. 1G, friction pads 44 sandwich ocular muscle hook handle 82 between them so that the ocular muscle hook does not freely slide in hook holder 40 but can be moved during use in an operation by application of a modicum of manual force. In the closed position shown in FIG. 1H, friction pads 44 sandwich hook handle 82 between them with force sufficient to lock the handle to the hook holder and operate to prevent motion of ocular muscle hook 80 relative to the friction pads. A modicum of manual force is a force that a surgeon using OSIN finds practical to apply to adjust position of muscle hook 80 during an ocular operation, such as a strabismus operation. A force sufficient to lock the handle to the muscle hook holder is a force which requires the surgeon to unlock the lock to enable adjustment of the position of the ocular muscle hook by application of the modicum of manual force.

FIGS. 2A-2F schematically show OSIN 20 being used in a strabismus resection operation on an eye 100, in accordance with an embodiment of the disclosure.

Figure 2A:
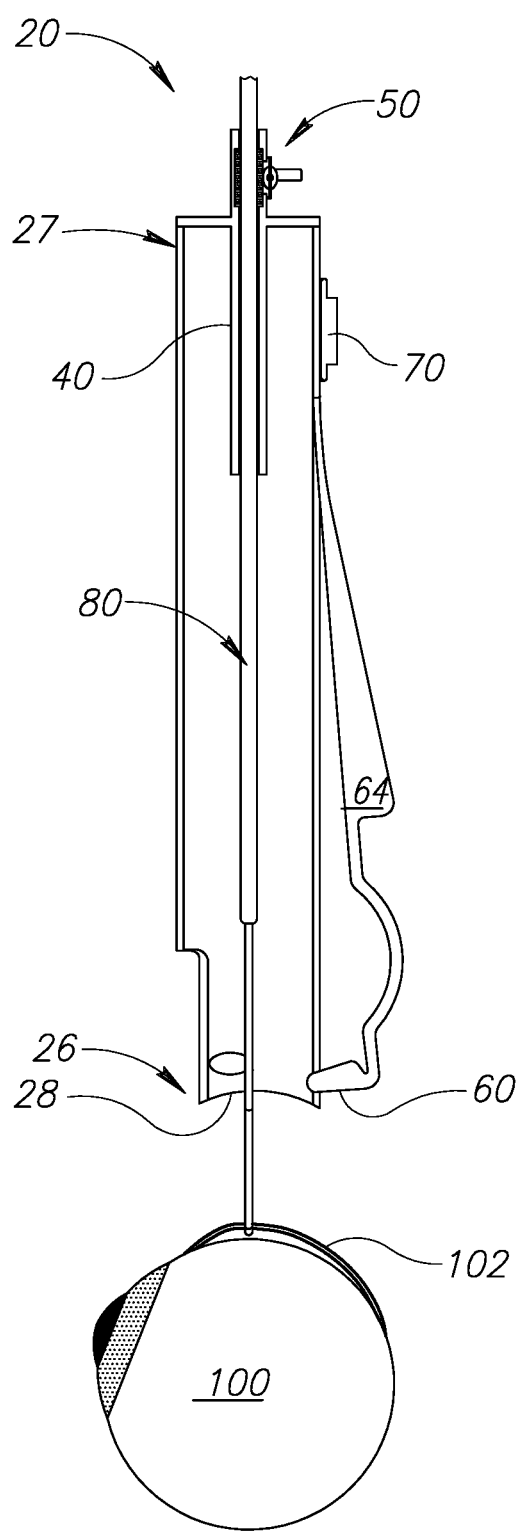
FIGS. 2A-2F schematically show a OSIN similar to that shown in FIGS. 1A-1H being used to perform a recession of a rectus muscle of an eye in which the rectus muscle is reinserted in a gluing operation near the muscle's native attachment location on the eye's sclera, in accordance with an embodiment of the disclosure.
Figure 2B:
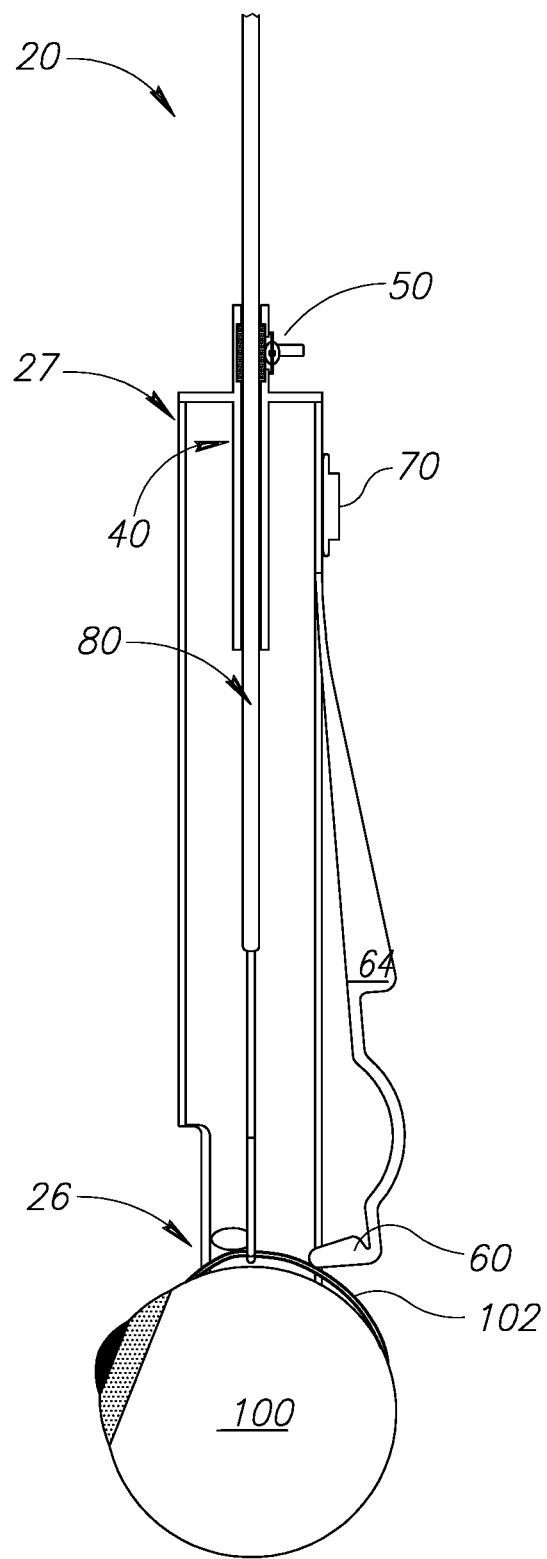

FIG. 2A schematically shows a cross-section of ocular muscle hook 80 mounted to OSIN 20 and extending out from bottom 26 of OSIN at an initial stage of the operation before OSIN is brought into contact with eye 100 and after the ocular muscle hook has engaged, by way of example, a superior rectus ocular muscle 102 of eye 100. In FIG. 2A lock 50 is in the open position and shank slider 70 is located near to top 27 of OSIN 20 and does not apply force to shank ramp 64. In FIG. 2B OSIN 20 has been lowered to contact eye 100 along bottom edge 28 of OSIN in preparation for raising ocular muscle hook 80 to elevate ocular muscle 102 away from eye 100. As noted above, bottom edge 28 may be configured to have a curvature that substantially matches curvature of eye 100 and may be covered with a suitable soft biocompatible elastomer that operates to prevent the eye from being injured by contact with the bottom edge.

Figures 2C, 2D:
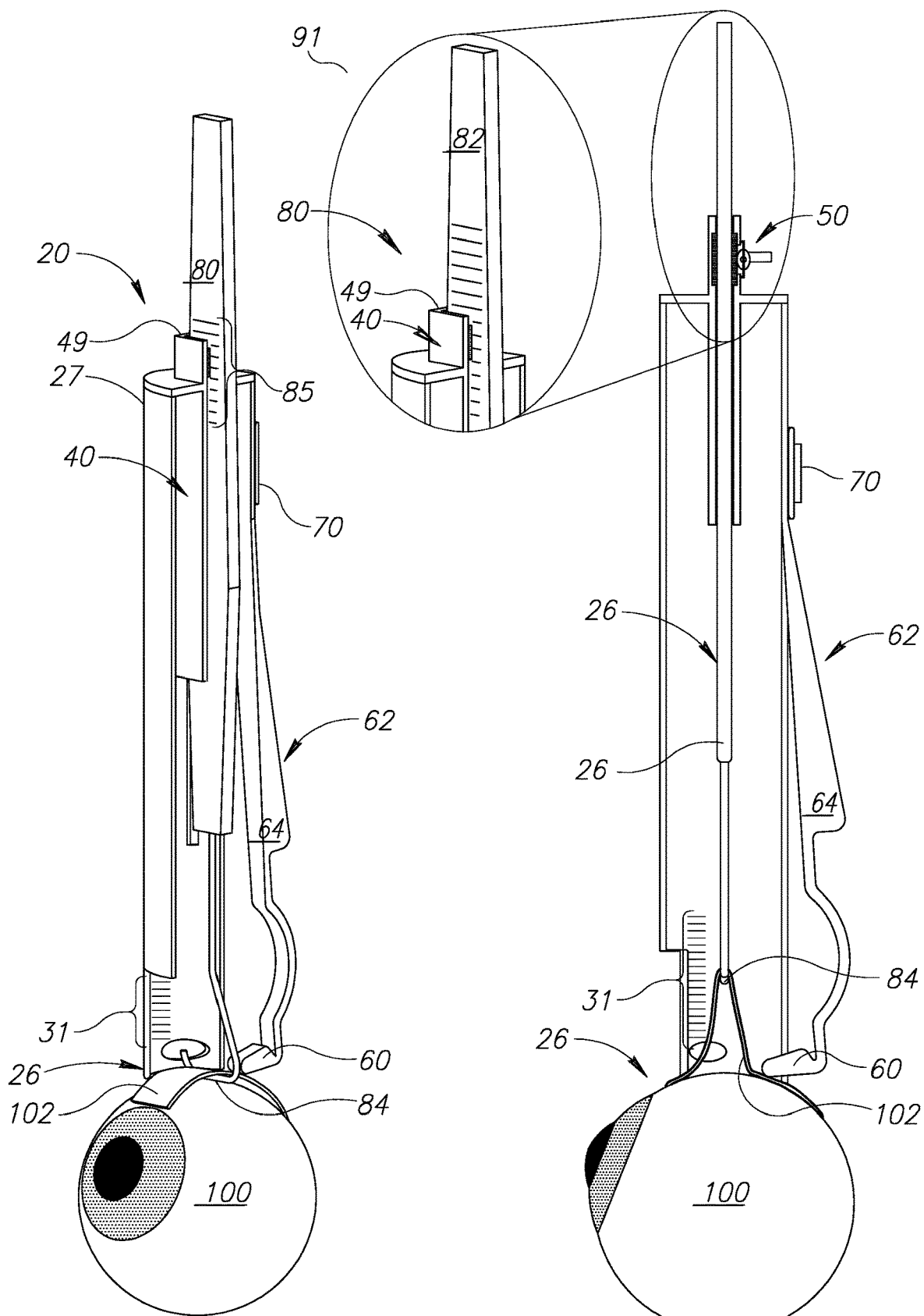

FIG. 2C schematically shows a perspective cutaway view of OSIN 20, ocular muscle hook 80, and eye 100 as shown in the cross-section view of FIG. 2B. FIG. 2C schematically shows graduation markings 31 on OSIN 20 and graduation markings 85 on ocular muscle hook 80. The figure illustrates the relation of graduation markings 31 to the position of hook 84 of ocular muscle hook 80, and the position of graduation markings 85 relative to edge 49 of ocular muscle hook holder 40.

FIG. 2D shows a cross-section of OSIN 20 and eye 100 after ocular muscle hook 80 has been raised to elevate superior rectus muscle 102 to a desired distance above eye 100. In accordance with an embodiment, an amount by which ocular muscle hook 80 has been raised and rectus muscle 102 elevated may be determined by referencing change of position of the ocular muscle hook to graduation markings 31 and/or 85. For example, an inset 91 in FIG. 2D shows a perspective view of ocular muscle hook handle 82, markings 85, and a portion of muscle hook holder 40 that includes edge 49, after ocular muscle hook 80 has been raised. Comparison of the position of graduation markings 85 relative to edge 49 in the inset with the position of markings 85 relative to edge 49 in FIG. 2C shows that ocular muscle hook 80 has been raised in FIG. 2D by five graduation markings relative to the position of the ocular muscle hook in FIG. 2C. Assuming by way of example that adjacent graduation markings 85 are spaced apart by 1 mm (millimeter), ocular muscle hook 80 has been raised by 5 mm in FIG. 2D relative to the position of ocular muscle hook 80 in FIG. 2C.

Figure 2E:
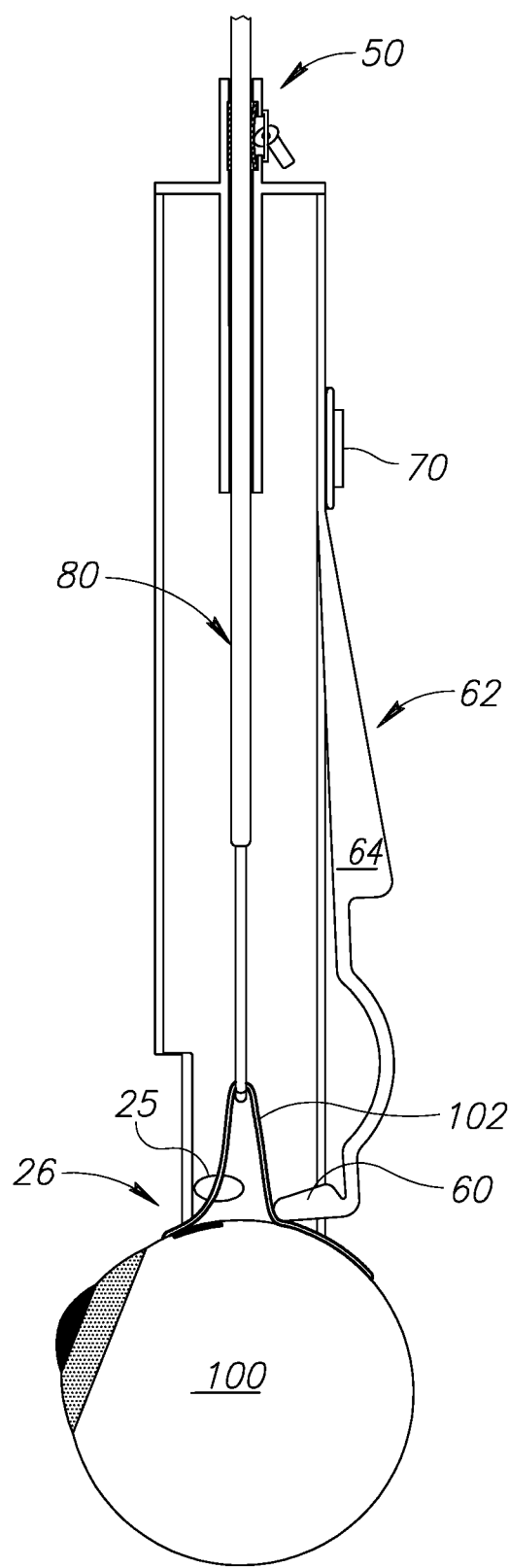

Following raising of ocular muscle hook 80 as shown in FIG. 2D, in FIG. 2E lock 50 is closed to lock ocular muscle hook 80 to OSIN 20 and lock rectus muscle 102 elevated to the desired distance and an amount of a topical biological glue is deposited on a reattachment region on the eye at which rectus muscle 102 is to be reattached. The glue may be deposited on the reattachment region by using a syringe introduced to the region through a glue injection port 25 to inject the glue onto the region. In FIG. 2E and figures that follow the deposited glue is schematically represented by a bold line 110. Following injection of glue 110, in FIG. 2F shank slider 70 is slid downward in a direction indicated by a block arrow 75 to press onto shank ramp 64 and rotate shank 62 clockwise in the plane of the figure to bring clamping foot 60 to press a region 103 of raised superior rectus muscle 102 into contact with glue 110 in the reattachment region on eye 100 and with a portion 104 of the rectus muscle at the native attachment region 105 of the rectus muscle. Clamping foot 60 is maintained in the position shown in FIG. 2F for sufficient time to allow glue 110 to set and bond regions 103 and 104 to each other and the reattachment region of eye 100. Following setting of glue 110, excess tissue of superior rectus muscle 102 folded into a loop 107 of muscle tissue 102 by operation of clamping foot 60 may be excised by cutting through the excess tissue with a scalpel, optionally using clamping foot 60 as a cutting anvil against which to cut the muscle tissue.

Figure 2F:
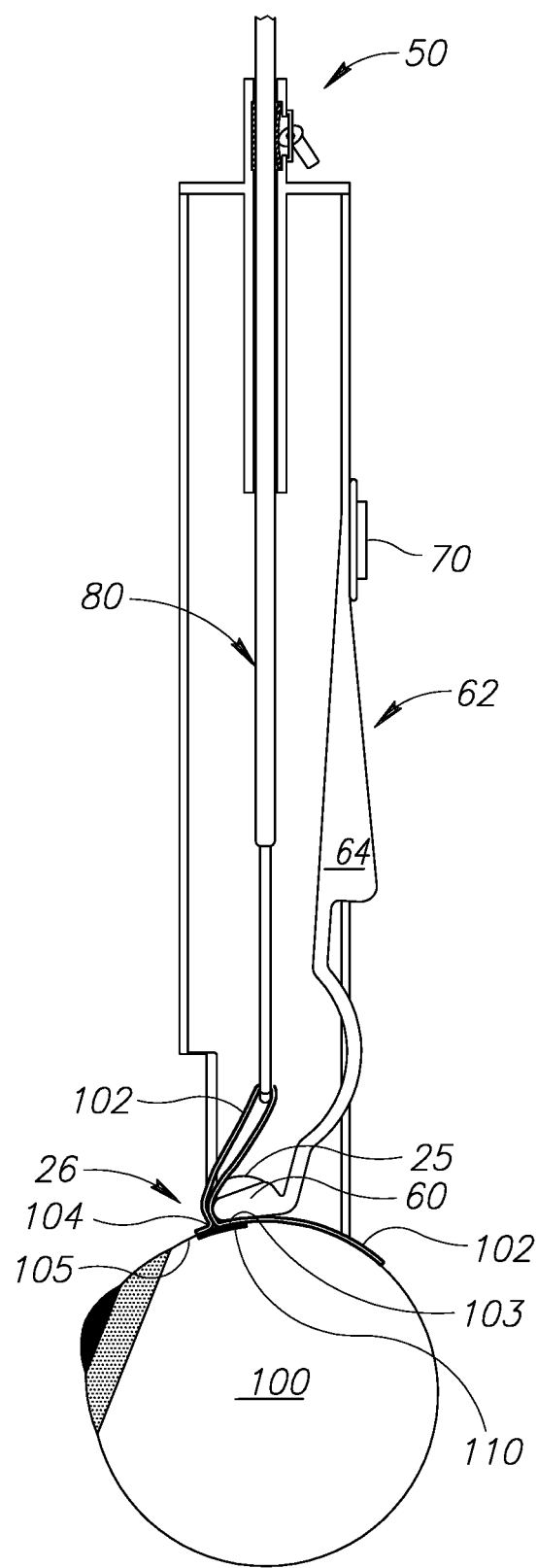
Figure 3A:
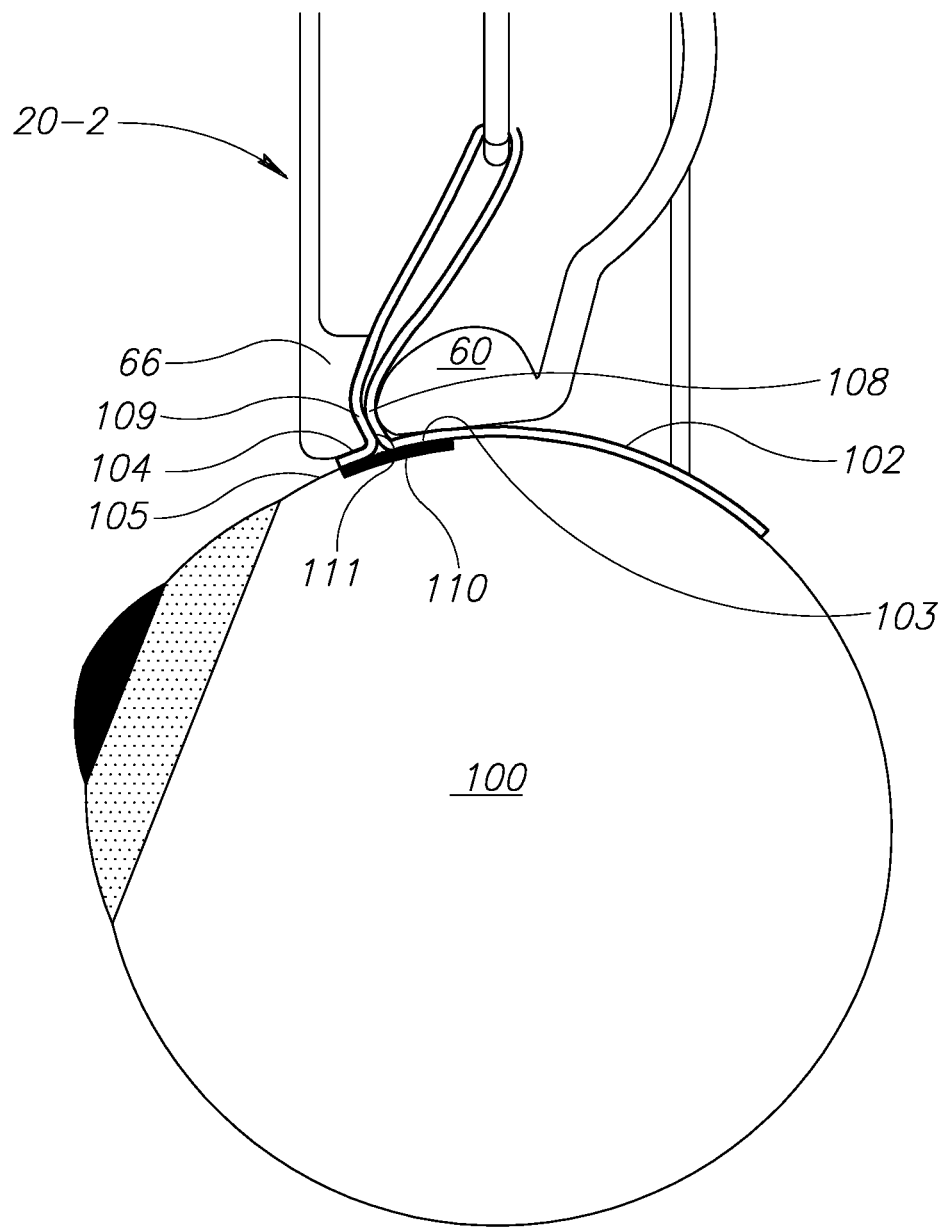
FIG. 3A schematically shows a clamping foot and a foot stop of comprised in a variation of the OSIN shown in FIGS. 2A-2F FIG. 3B schematically shows a clamping foot and a foot configured to reinsert by stapling an ocular muscle in a strabismus resection operation in accordance with an embodiment of the disclosure.

In an embodiment, an OSIN similar to OSIN 20 may be configured to have a foot stop against which a clamping foot, such as a clamping foot 60 shown in FIG. 2F, may compress together portions of ocular muscle tissue when clamping a region of an ocular muscle to glue the region to a gluing region of an eye. By way of example FIG. 3A schematically shows a cross-section of a portion of an OSIN 20-2 having a foot stop 66 against which clamping foot 60 compresses portions 108 and 109 of superior rectus muscle 102 together when gluing a region 103 of the rectus muscle to eye 100 in a neighborhood of native attachment region 105 of the rectus muscle. As schematically shown in FIG. 3A, foot stop 66 may aid in sandwiching a quantity 111 of glue 110 between muscle portions 108 and 109 and bonding the portions together to provide a strong anchor of muscle region 103 of rectus muscle 102 to eye 100.

Figure 3B:
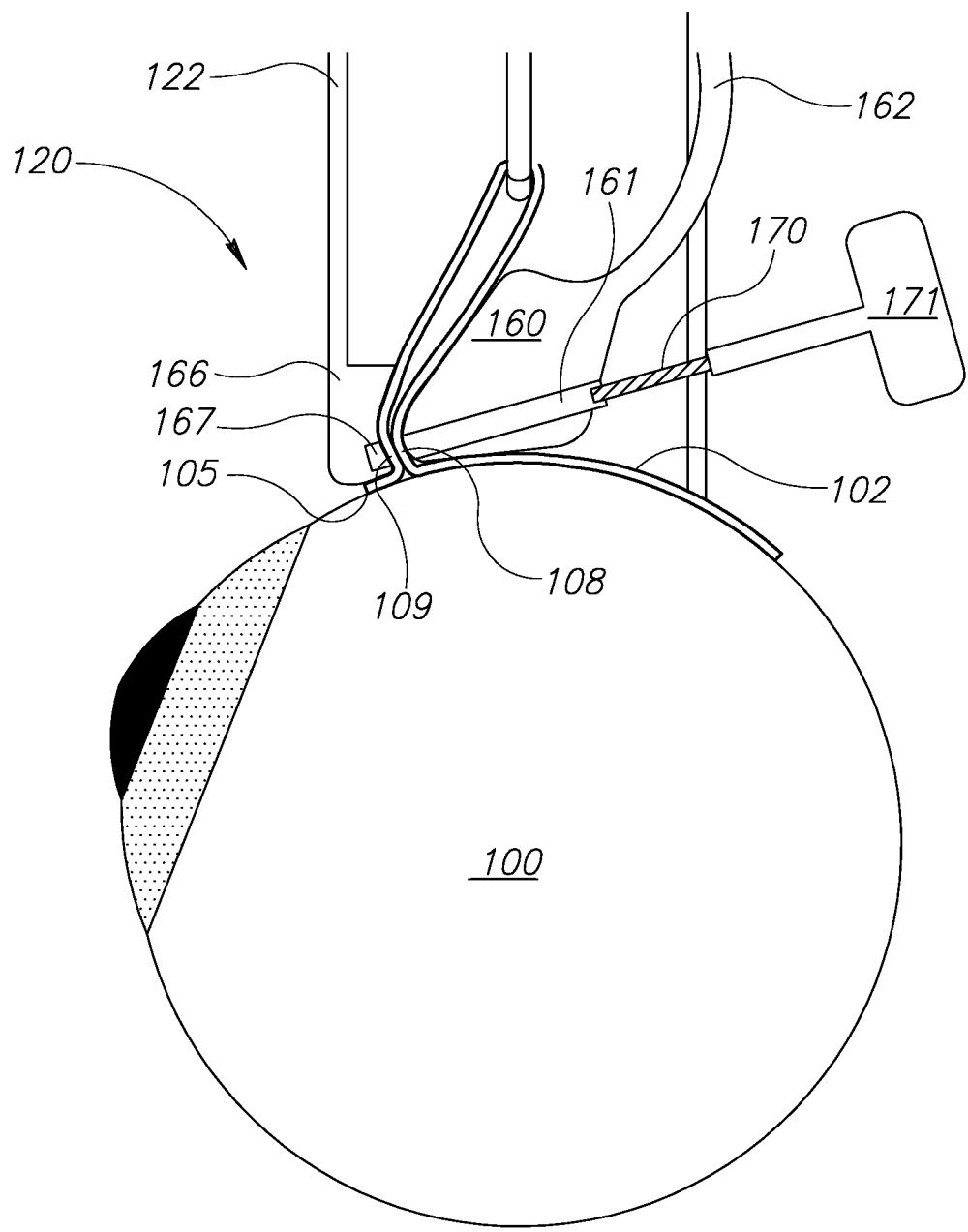

In an embodiment an OSIN may comprise a clamping foot and foot stop that are configured to staple portions of an ocular muscle together to perform a strabismus resection operation in accordance with an embodiment of the disclosure. FIG. 3B schematically shows a cross-section of a portion of an OSIN 120 having a support housing 122, and a clamping foot 160 and matching foot stop 166 configured to staple together portions of an ocular muscle in a resection operation. By way of example OSIN 120 is shown stapling portions 108 and 109 of superior rectus muscle 102 together.

Clamping foot 160 is formed having a staple channel 161 for receiving a staple 170 pushed into the channel by a staple hammer 171 and directing the staple to a recess 167 formed in foot stop 166 and shaped to operate as a crimping recess. As staple hammer 171 is operated to push staple 170 into and through channel 161, legs (not shown) of staple 170 penetrate muscle regions 108 and 109 and are forced into crimping recess 167 where the staple legs are bent to staple regions 108 and 109 together. In an embodiment, staple hammer 171 may hold staple 170 by a magnetic force or by an adhesive applied to a region of the staple hammer and be manually operated to push staple 170 through staple channel 161 and muscle regions 108 and 109. Optionally, staple hammer 171 is hinged to support housing 122 of OSIN 120 or to a portion of shank 162 to which clamping foot 160 is attached.

Figure 4A:
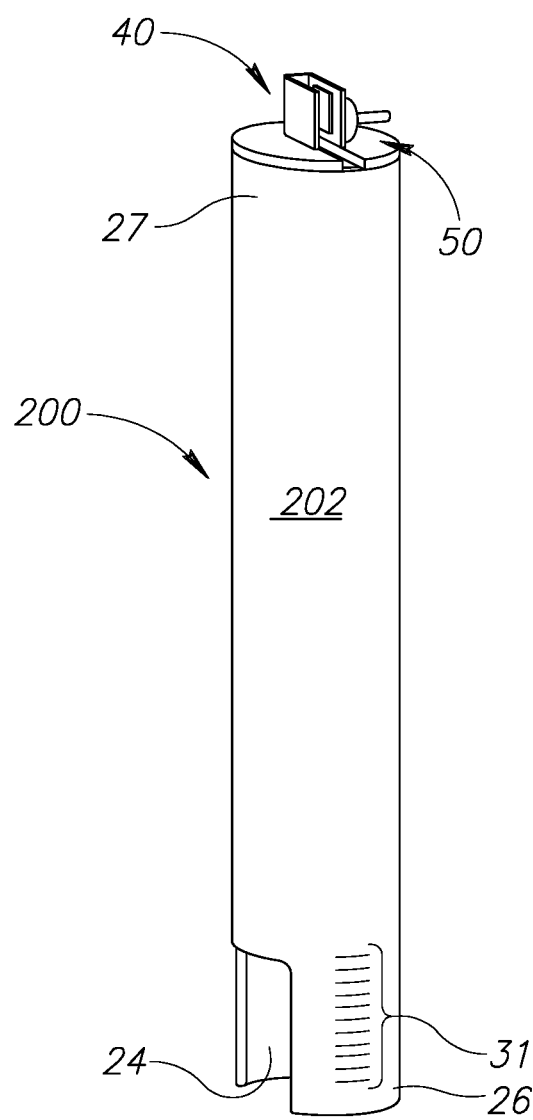
FIGS. 4A-4H schematically show an OSIN configured to reinsert an ocular muscle in a strabismus operation by suturing and operation of the OSIN in resecting a superior rectus muscle of an eye, in accordance with an embodiment of the disclosure.
Figure 4B:
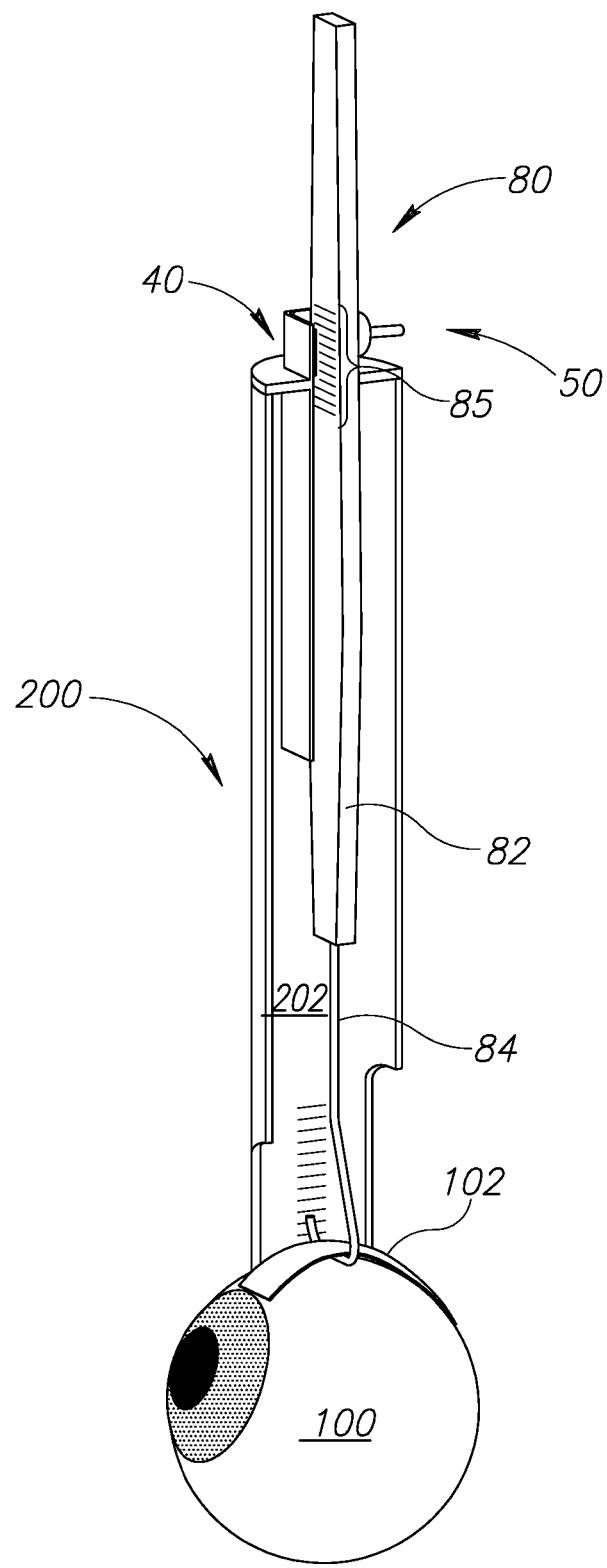
Figure 4C:
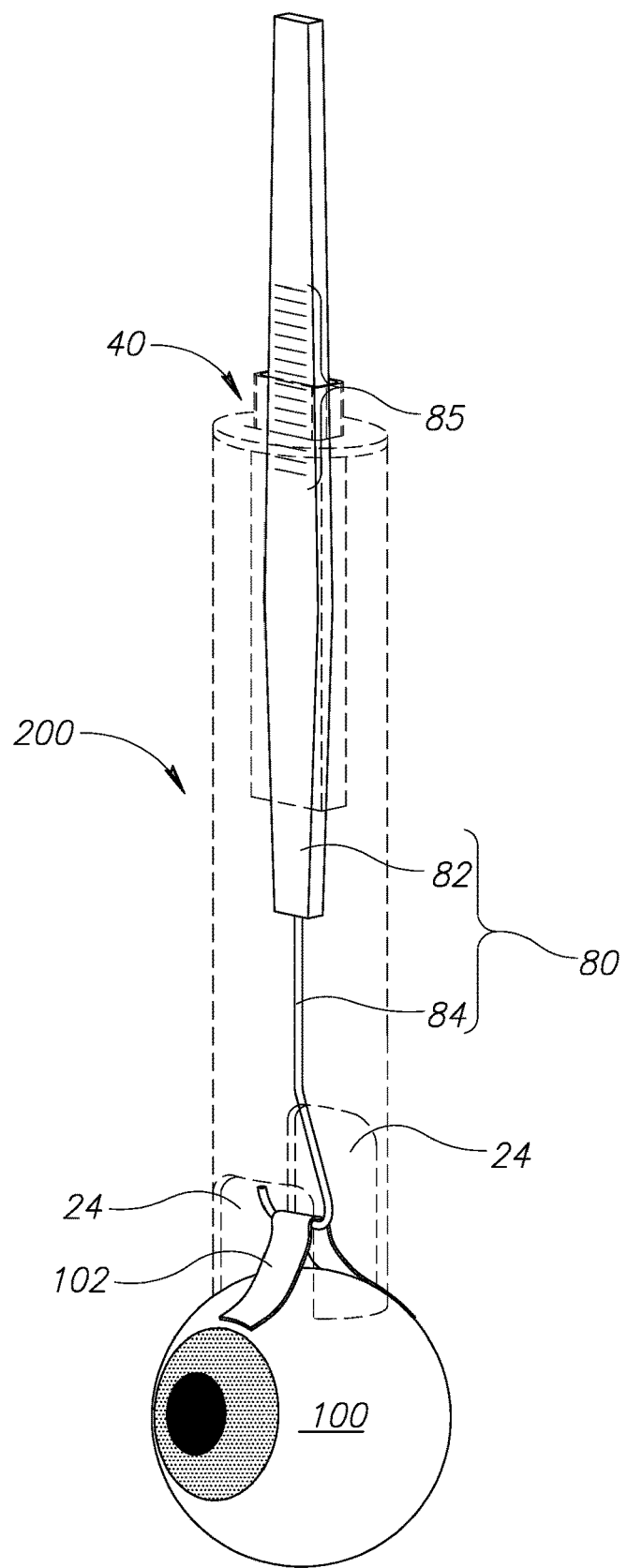
Figure 5A:
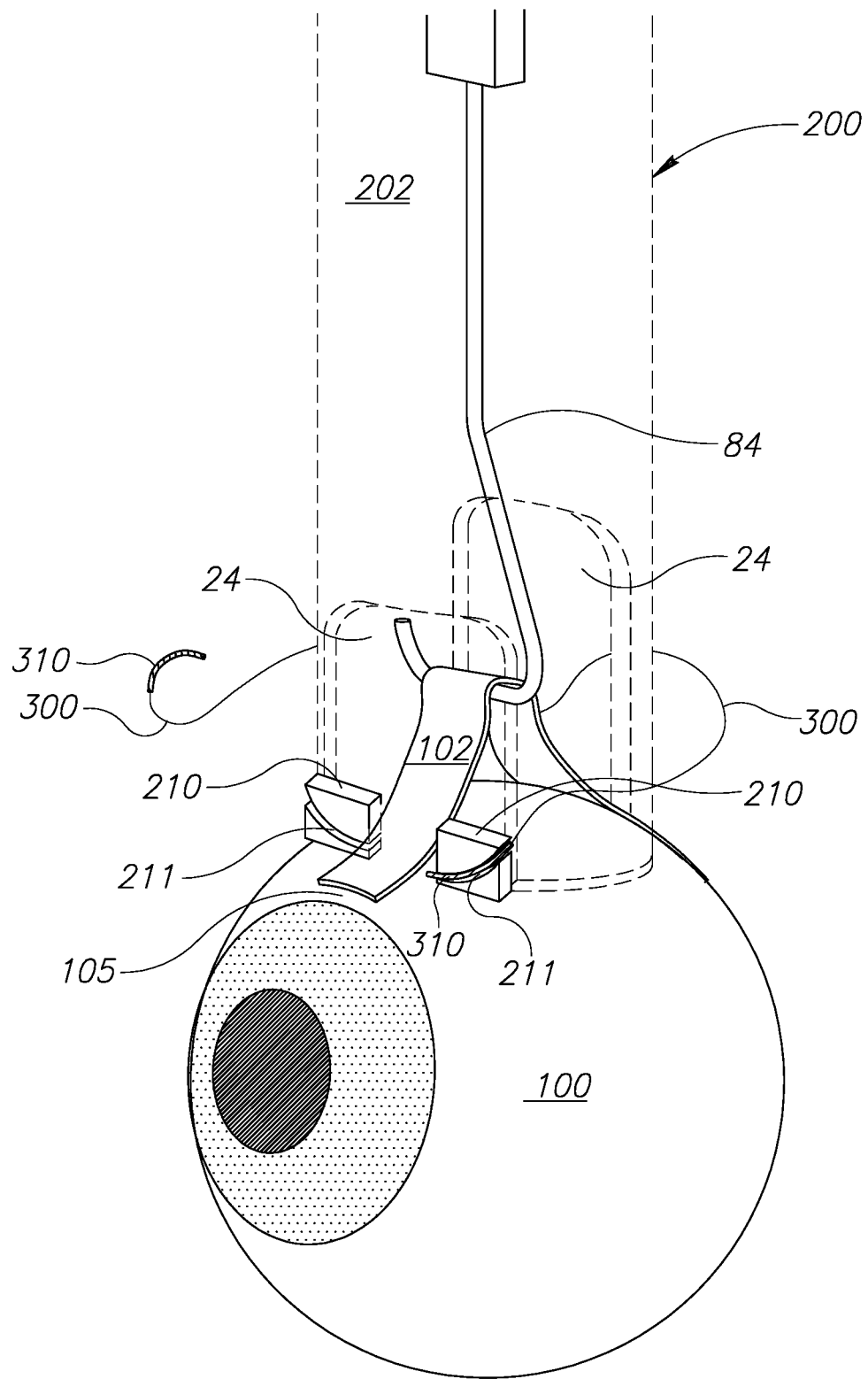
FIGS. 5A and 5B schematically show features of variations of an OSIN, in accordance with an embodiment of the disclosure.
Figure 5B:
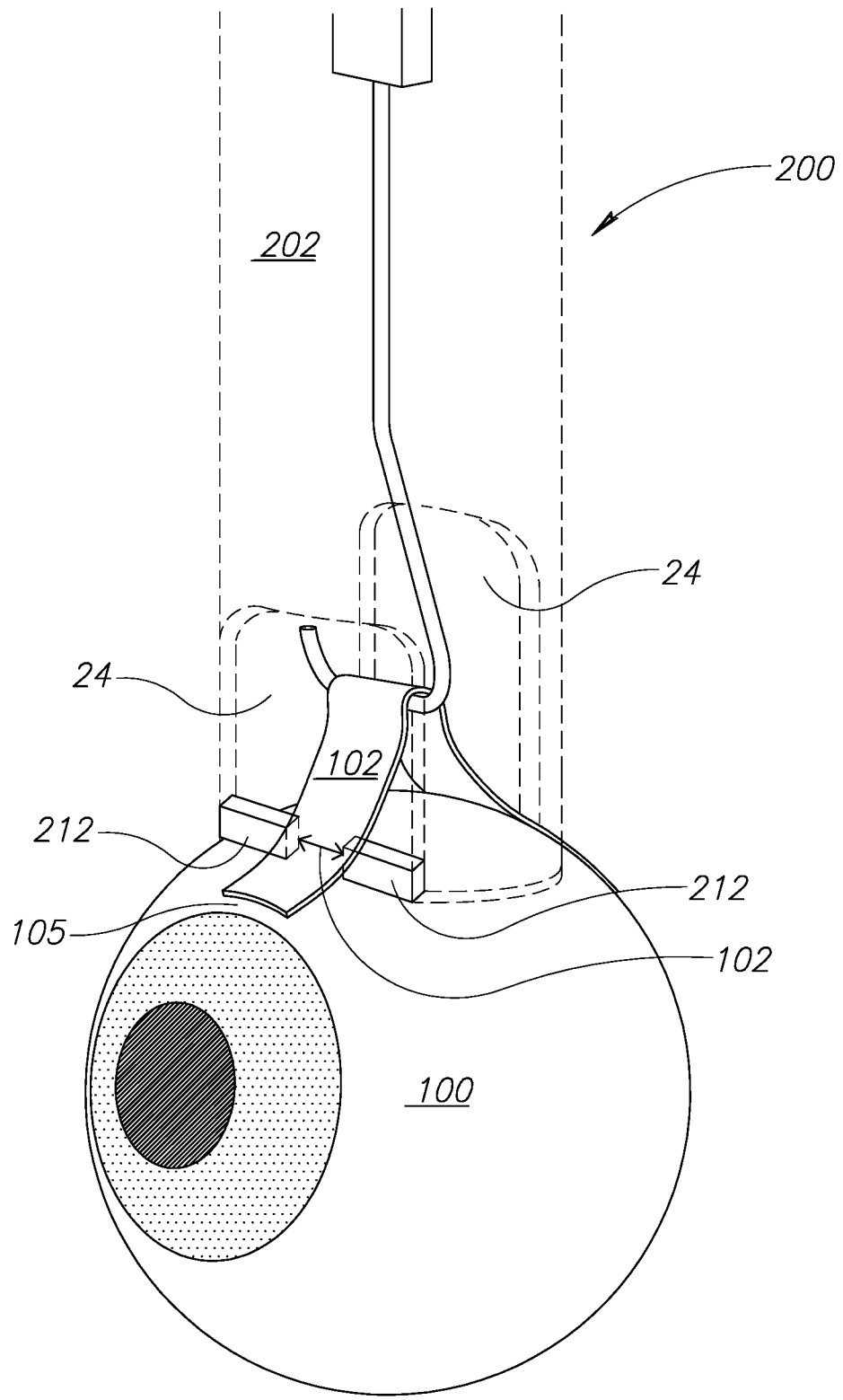

FIGS. 4A-4C schematically show a perspective view, a perspective cutaway view, and a transparent "see-through" view respectively of an OSIN 200 configured to be used in a strabismus operation in which an ocular muscle is reattached to an eye by suturing, in accordance with an embodiment of the disclosure.

OSIN 200 optionally comprises a support housing 202, having a muscle hook holder 40 optionally protruding from a cap 41 at a top end 27 of the support housing, a lock 50 attached to the holder, and at a bottom end 26 of the housing optionally two access apertures 24 and graduation markings 31. Cut away view of OSIN 200 in FIG. 4B schematically shows OSIN 200 positioned on an eye 100 and holding a ocular muscle hook 80 optionally comprising a hook 84 and a handle 82 having graduation markings 85. In the figure ocular muscle hook 80 has been manipulated to engage superior rectus muscle 102 of eye 100. In see-through image of OSIN 200 shown in FIG. 4C ocular muscle hook 80 has been raised to elevate rectus muscle from eye 100 by a desired distance.

FIGS. 4D-4H schematically illustrate OSIN 200 being used to perform a strabismus resection operation on rectus muscle 102 after the muscle has been elevated as shown in FIG. 4C, in accordance with an embodiment of the disclosure.

Figure 4D:
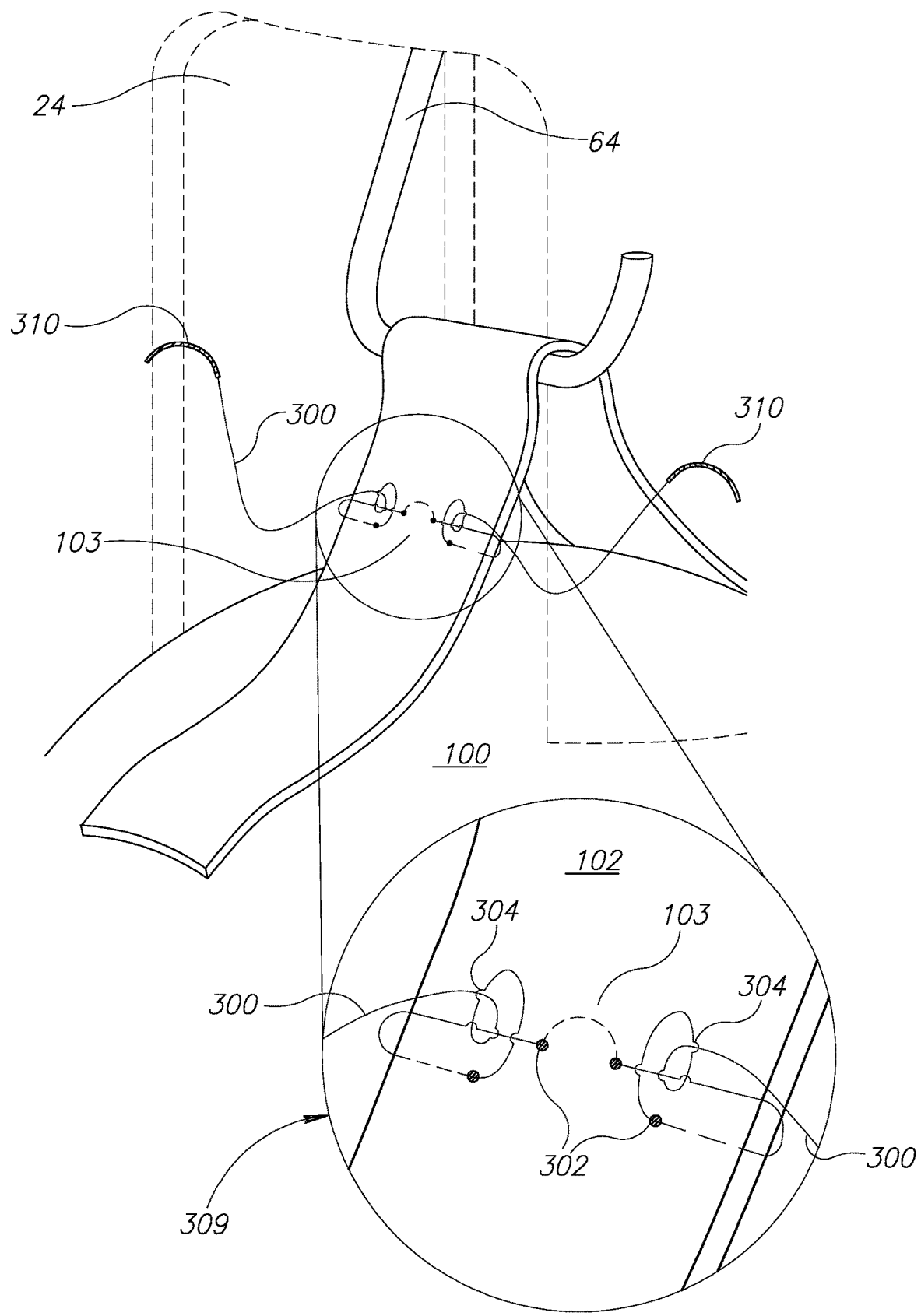

FIG. 4D schematically shows a posterior view of a portion of eye 100 and superior rectus muscle 102 following securing a region 103 of muscle 102 with a double armed surgical suture 300 having a spatulated needle 310 at each end of the suture. Lengths of suture 300 that lie on top side of muscle 102 are shown in solid lines. Lengths of suture 300 that lie on an underside of muscle 102 are shown in dashed lines. Regions of muscle 102 through which the suture passes from one side to the other side of the muscle are indicated by solid circles 302. A loop 304 in a section of suture 300 indicates that the section lies over a section of suture 300 that passes through the loop. An inset 309 schematically shows an enlarged view of suture 300 that secures muscle 102.

Figure 4E:
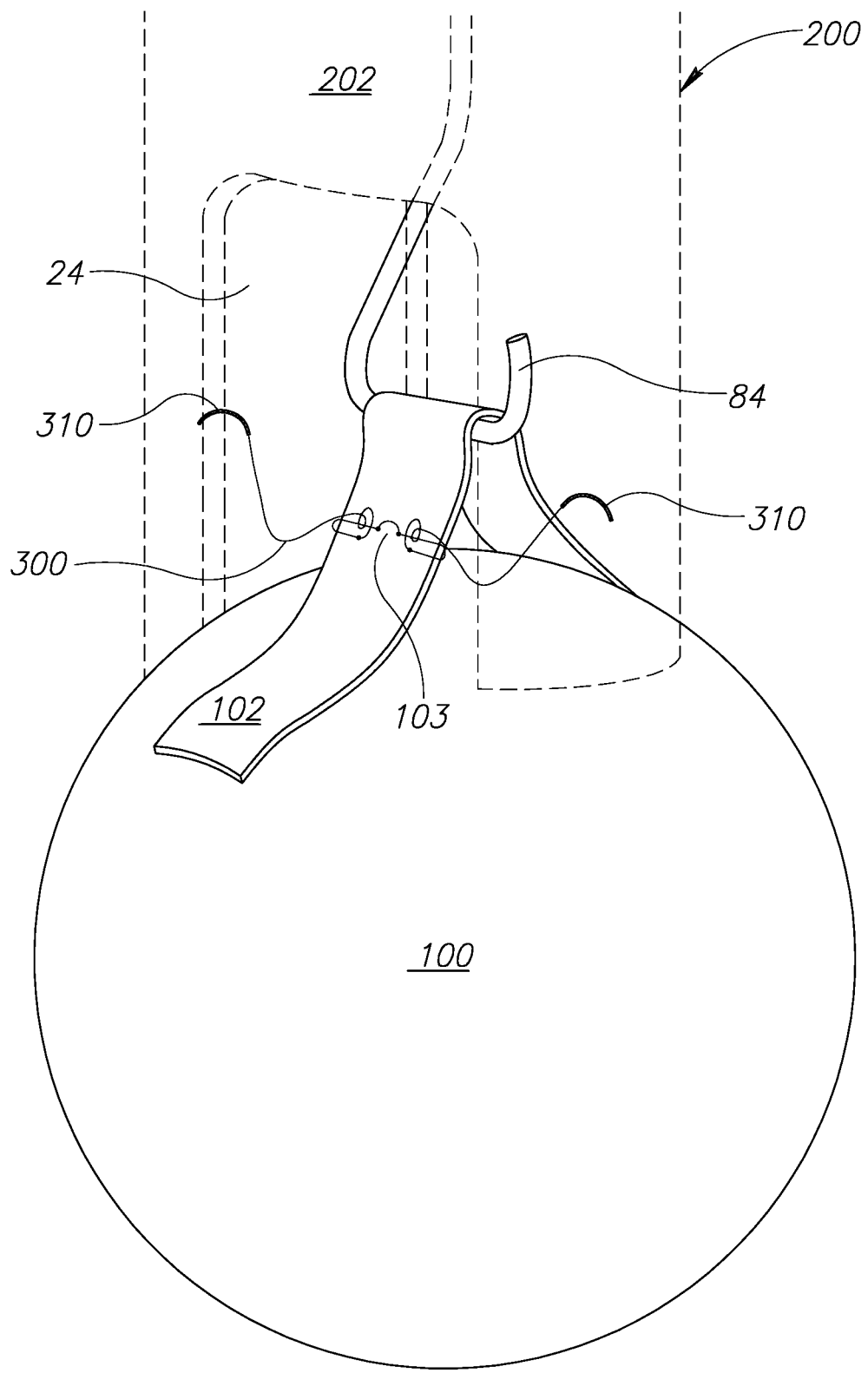
Figure 4F:
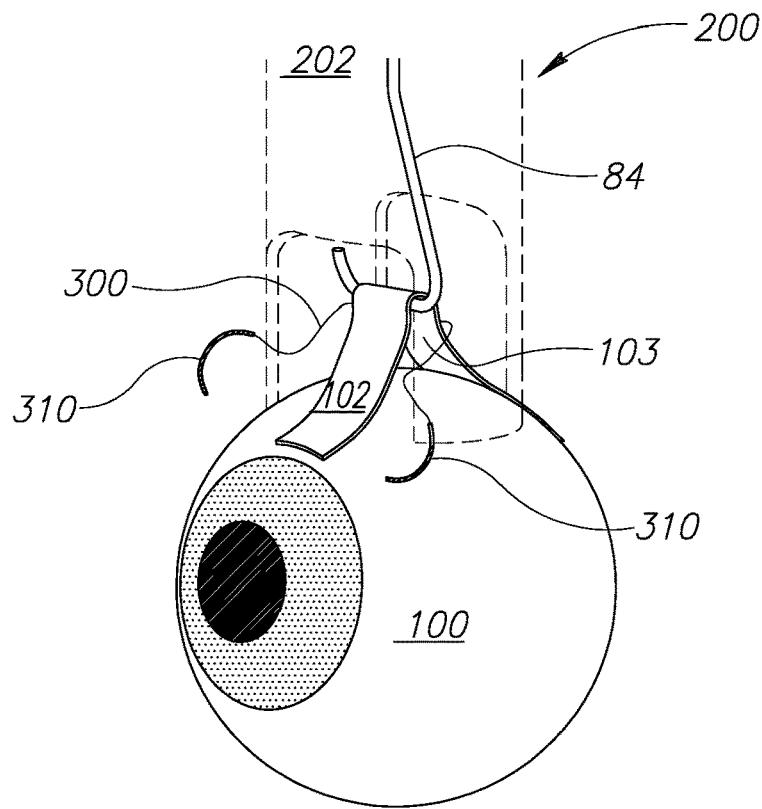
Figure 4G:
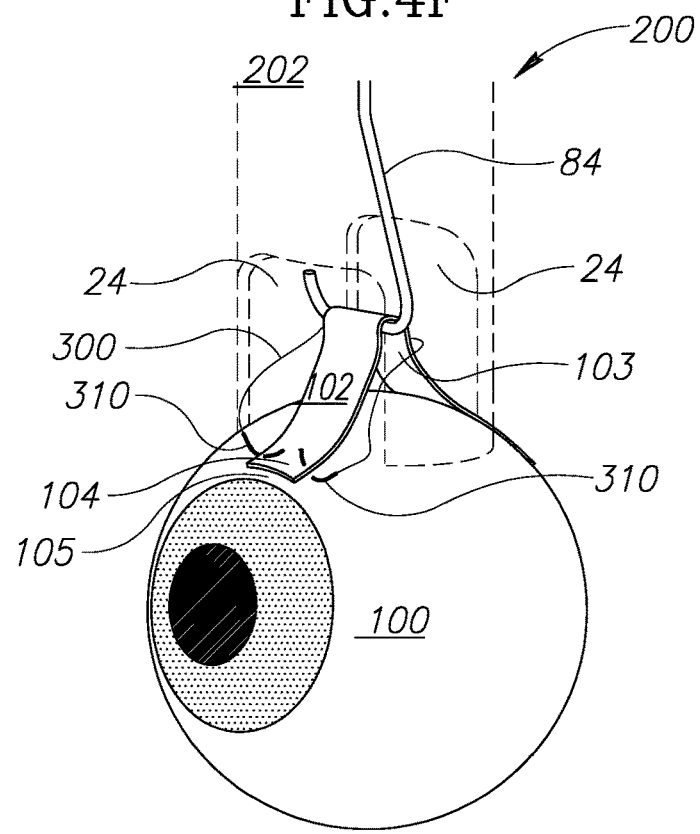
Figure 4H:
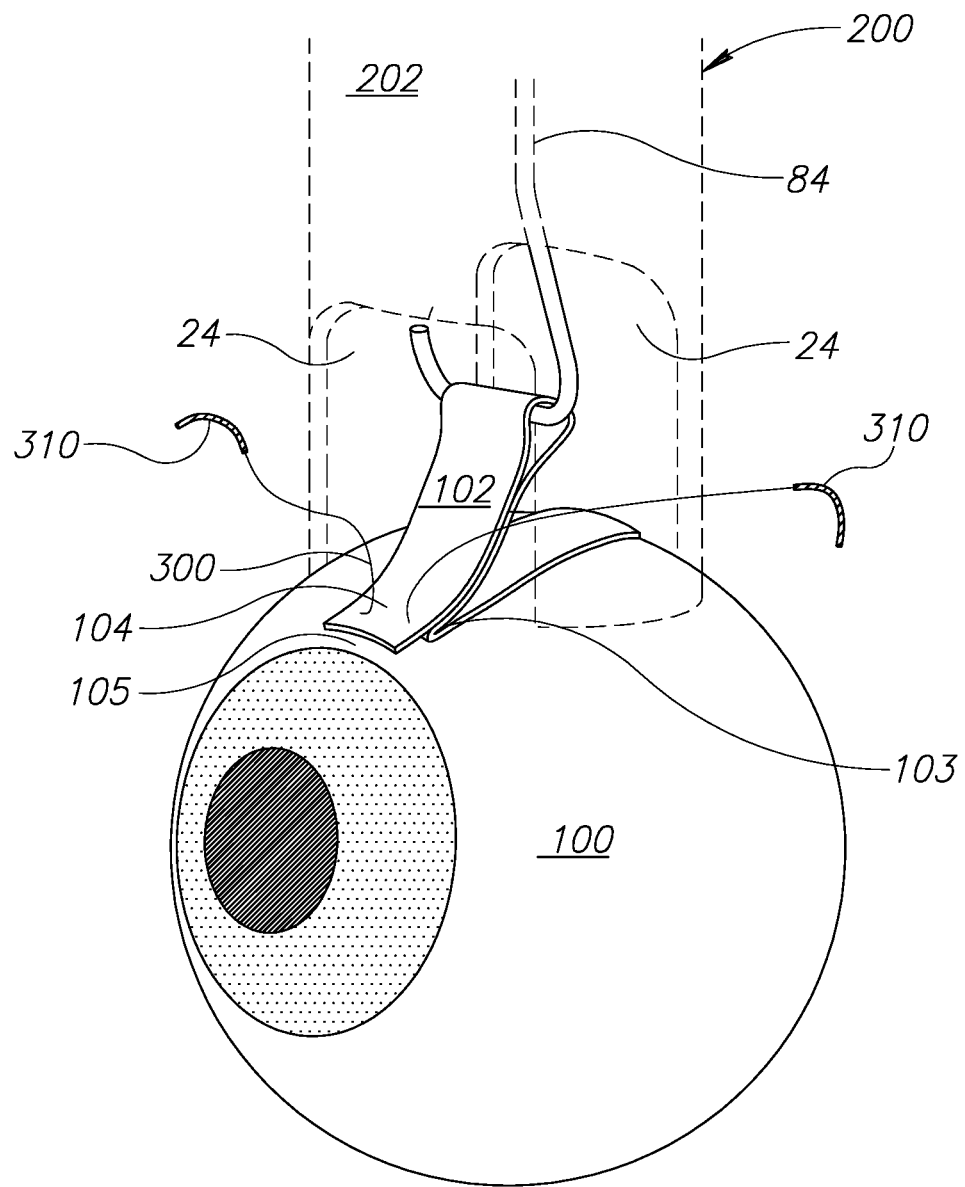

FIG. 4E schematically shows a perspective posterior view of all of eye 100, a portion of OSIN 200, and superior rectus muscle 102 following securing region 103 of muscle 102 with double armed suture 300. FIG. 4F schematically shows eye 100 and muscle 102 shown in FIG. 4E from a perspective anterior view of eye 100. FIG. 4G schematically shows spatula needles 310 being used to puncture the top tissue layer, the sclera (not separately shown), of eye 100 and a region 104 of rectus muscle 102 to suture region 103 of the muscle to the sclera (not shown) near the native attachment region 105 of the muscle. Following puncturing and threading suture 300 through the sclera, suture 300 is drawn taut as schematically shown in FIG. 4H to pull and suture region 103 to region 104 and to region 105 the eye's sclera. After being drawn taut, suture 300 may be knotted and excess tissue from muscle 102 excised to complete the resection operation.

Care is advantageously taken when using a spatula needle 310 to suture muscle 102 to eye 100 to prevent the spatula needle from puncturing through the eye's sclera and damaging an internal tissue of the eye. In an embodiment an OSIN, such as OSIN 200 may be configured as schematically shown in FIG. 5A having needle guides 210, each formed having a guide slot 211 curved to match the curve of a spatula needle 310 and into which the spatula needle may be inserted. Each needle guide 210 is positioned to orient its guide slot 211 so that the inserted needle 310 may be guided along the slot to penetrate, move through, and exit the sclera along a curved path in the sclera having a maximum depth that is less than the thickness of the sclera and advantageous for attaching muscle 102 to the eye without perforating the eye's globe.

In an embodiment an OSIN, such as OSIN 200, may have a pair of muscle stops 212, as schematically shown in FIG. 5B, that are formed as a part of housing 202 to aid in positioning the housing during a strabismus operation. The muscle stops are located, optionally inside housing 202, so they may be positioned, by way of example, over rectus muscle 102 before the muscle is elevated by ocular muscle hook 80. Stops 212 are separated by a distance indicated by a double arrowhead line labeled "D", that allows ocular muscle hook 80 to forcibly pull muscle 102 through space D when elevating the muscle. After muscle 102 is elevated, muscle stops 212 lie under the muscle and behind native attachment region 105 of the muscle. The stops then operate to prevent displacement of housing 202 in a direction towards native attachment region 105 beyond the native attachment region. In an embodiment distance D is determined so that the ends of muscle stops 212 that face each other catch edges of muscle 102. By way of numerical example D may be between about 3 mm to about 3.5 mm.

Figure 6A:
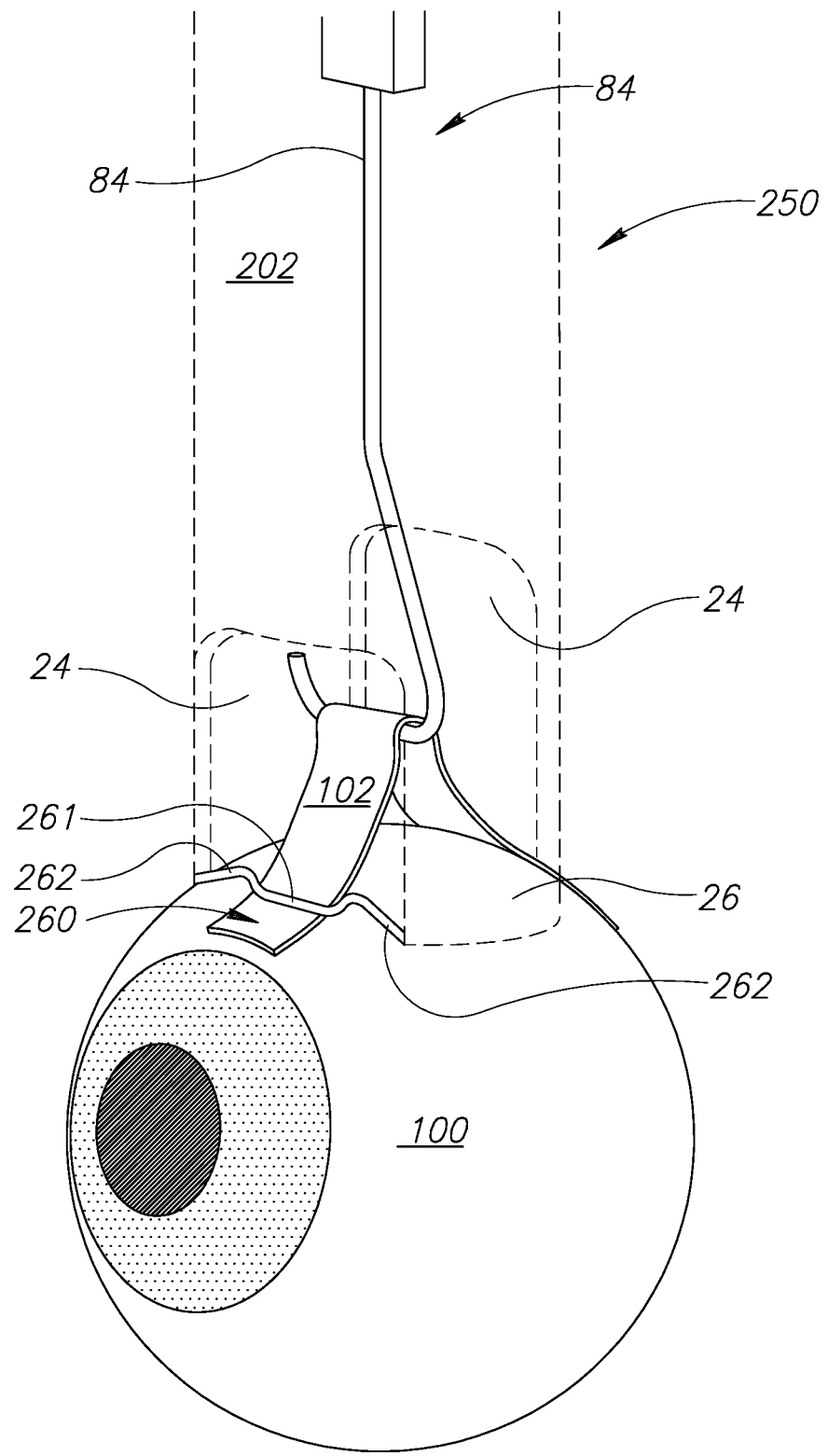
FIGS. 6A and 6B schematically show operation of a variation of an OSIN, in accordance with an embodiment of the disclosure.
Figure 6B:
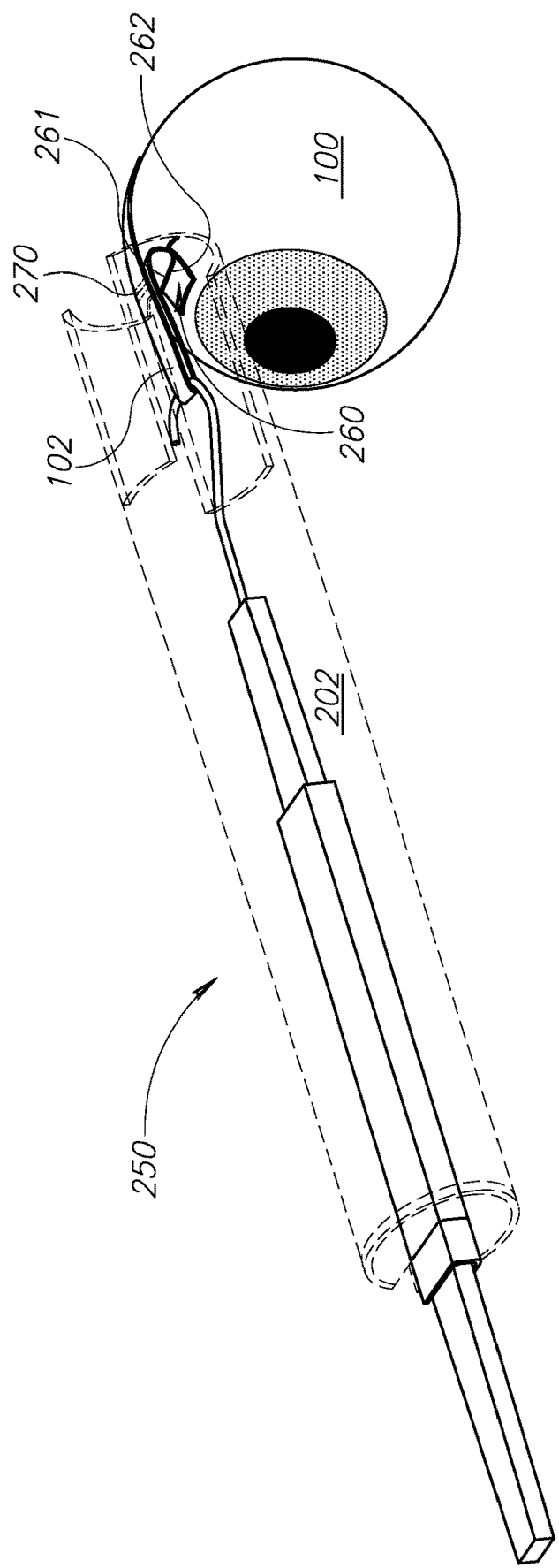

FIG. 6A schematically shows an OSIN 250 in accordance with an embodiment that is similar to OSIN 200 but comprises a roll-bar 260 which bridges aperture 24 at bottom 26 of support housing 202 near to or at bottom edge 28, in accordance with an embodiment of the disclosure. Roll bar 260 optionally has an omega-like shape comprising a base segment 261 and two raised wing segments 262. By way of example OSIN 250 is shown in FIG. 6A being used with ocular muscle hook 80 to perform a strabismus resection on rectus muscle 102. After ocular muscle hook 80 is operated to elevate muscle 102 as shown in FIG. 6A, OSIN 250 may be rotated around roll bar 260 optionally by about 90° as shown in FIG. 6B to trap a loop of muscle 102 on base segment 261 between wing segments 262. Opposite tissue regions of the loop may be joined, for example by suturing, gluing and/or stapling. together along a region indicated by dashed lines 270 to shorten the length of muscle tissue in muscle 102 and correct for strabismus.

There is therefore provided according to an embodiment of the disclosure an apparatus for performing an ocular surgery, the apparatus comprising: a support housing having a bottom configured to be positioned on the sclera of an eye during performance of an ocular surgery; a muscle hook holder connected to the support housing and configured to hold an ocular muscle hook so that the ocular muscle hook may be translatable to elevate an ocular muscle away from the eye during performance of the surgery; and a set of graduation markings on the support housing useable to determine a distance that the ocular muscle hook may be translated to elevate the ocular muscle. Optionally, the set of graduation markings is located near the bottom of the housing. Optionally, adjacent graduation markings are spaced apart by a same distance.

In an embodiment, the housing is formed having at least one access aperture through which a tool to perform the surgery is introduced and manipulated.

In an embodiment, the muscle hook holder is configured to hold the ocular muscle hook with force that operates to prevent unwanted motion of the ocular muscle hook during performance of the surgery but enables application of a modicum of force to adjust the position of the ocular muscle hook during the surgery. Optionally, the muscle hook holder comprises at least one friction pad that contacts the ocular muscle hook and applies the force to prevent the unwanted motion of the ocular muscle hook.

In an embodiment, the muscle hook holder comprises a lock operable to be locked and apply force to the ocular muscle hook sufficient to lock the ocular muscle hook to the muscle hook holder. Optionally, the lock comprises a locking wheel rotatable to lock the lock. Optionally, the muscle hook holder comprises at least one friction pad that contacts the ocular muscle hook and when rotated the locking wheel contacts and presses on a friction pad of the at least one friction pad to lock the lock.

In an embodiment the apparatus comprises a roll bar at the bottom of the housing about which the housing is rotatable to pull the elevated muscle to form a loop of muscle tissue having two regions of muscle tissue pressed to each other, so that the pressed muscle regions can be joined together to perform a resection of the ocular muscle.

In an embodiment the apparatus comprises at least one needle guide having a guide slot curved to match the curve of a needle used to suture a region of the ocular muscle to the sclera and along which needle guide the needle is guidable to suture the region of the ocular muscle to the sclera without perforating the eye globe.

In an embodiment the apparatus comprises at least one muscle stop located at the bottom of the housing which when the bottom is placed on the sclera operates to prevent displacement of the housing in a direction towards a native attachment region of the ocular muscle beyond the native attachment region.

In an embodiment, the housing comprises a clamping foot operable to clamp a region of an ocular muscle to the sclera.

There is further provided according to an embodiment of the disclosure an apparatus for performing an ocular surgery, the apparatus comprising: a support housing having a bottom configured to be placed on the sclera of an eye during performance of an ocular surgery; a muscle hook holder connected to the support housing and configured to hold an ocular muscle hook so that the ocular muscle hook is translatable to elevate an ocular muscle away from the eye during performance of the surgery; and a clamping foot operable to clamp a region of the ocular muscle to the sclera. Optionally or additionally, the clamping foot is formed at an end of a shank coupled to the support housing and rotatable to a position that clamps a region of the ocular muscle to the sclera. Optionally, the shank comprises a ramp to which force is applicable to rotate the shank. Optionally, the housing comprises a shank slider operable to be moved along the housing to apply force to the ramp to rotate the shank. Optionally, the housing is formed having a slot and the shank slider having a snap clip which is snap clipped into the slot to mount the shank slider to the housing.

In an embodiment, the housing comprises a foot stop to which the clamping foot is pressable by rotation of the shank. In an embodiment, the housing is formed having at least one glue injection port through which a topical biological glue is injectable onto the sclera.

There is further provided according to an embodiment of the disclosure an ocular muscle hook comprising graduation markings that are referenceable to determine a distance to which the ocular muscle hook is translated to elevate an ocular muscle during an ocular surgery.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments of the disclosure. Some embodiments utilize only some of the features or possible combinations of the features. Variations of embodiments of the disclosure that are described, and embodiments of the disclosure comprising different combinations of features noted in the described embodiments, will occur to persons of the art. The scope of the disclosure is limited only by the claims.

The invention claimed is:

1. An apparatus for performing an ocular surgery, the apparatus comprising:
 a support housing having a bottom configured to be positioned on the sclera of an eye during performance of an ocular surgery;
 a muscle hook holder connected to the support housing and configured to hold an ocular muscle hook so that the ocular muscle hook is translatable to elevate an ocular muscle away from the eye during performance of the surgery;
 a set of graduation markings on the support housing useable to determine a distance that the ocular muscle hook is translated to elevate the ocular muscle; and
 at least one needle guide having a guide slot curved to match the curve of a needle used to suture a region of the ocular muscle to the sclera and along which needle guide the needle is guidable to suture the region of the ocular muscle to the sclera without perforating the eye globe.

2. The apparatus of claim 1, wherein the set of graduation markings is located near the bottom of the housing.

3. The apparatus of claim 2, wherein adjacent markings are spaced apart by a same distance.

4. The apparatus of claim 1, wherein the housing is formed having at least one access aperture through which a tool to perform the surgery is introduced and manipulated.

5. The apparatus of claim 1, wherein the muscle hook holder is configured to hold the ocular muscle hook with force that operates to prevent unwanted motion of the ocular muscle hook during performance of the surgery but enables application of a modicum of force to adjust position of the ocular muscle hook during the surgery.

6. The apparatus of claim 5, wherein the muscle hook holder comprises at least one friction pad that contacts the ocular muscle hook and applies the force to prevent the unwanted motion of the ocular muscle hook.

7. The apparatus of claim 1, wherein the muscle hook holder comprises a lock operable to be locked and apply force to the ocular muscle hook sufficient lock the ocular muscle hook to the muscle hook holder.

8. The apparatus of claim 7, the lock comprises a locking wheel rotatable to lock the lock.

9. The apparatus of claim 8, wherein the muscle hook holder comprises at least one friction pad that contacts the ocular muscle hook and when rotated the locking wheel contacts and presses on a friction pad of the at least one friction pad to lock the lock.

10. The apparatus of claim 1, comprising a roll bar at the bottom of the housing about which the housing is rotatable to pull the elevated muscle to form a loop of muscle tissue having two regions of muscle tissue pressed to each other, so that the pressed muscle regions can be joined together to perform a resection of the ocular muscle.

11. The apparatus of claim 1, comprising at least one muscle stop located at the bottom of the housing which when the bottom is placed on the sclera operates to prevent displacement of the housing in a direction towards a native attachment region of the ocular muscle beyond the native attachment region.

12. The apparatus of claim 1, wherein the housing comprises a clamping foot operable to clamp a region of an ocular muscle to the sclera.

13. The apparatus of claim 1, wherein the housing is formed having at least one glue injection port through which a topical biological glue is injectable onto the sclera.

14. An apparatus for performing an ocular surgery, the apparatus comprising:
 a support housing having a bottom configured to be placed on the sclera of an eye during performance of an ocular surgery;
 a muscle hook holder connected to the support housing and configured to hold an ocular muscle hook so that the ocular muscle hook is translatable to elevate an ocular muscle away from the eye during performance of the surgery;
 a clamping foot operable to clamp a region of the ocular muscle to the sclera, wherein the clamping foot is formed at an end of a shank coupled to the support housing and rotatable to a position that clamps a region of the ocular muscle to the sclera, said shank comprises a ramp to which force is applicable to rotate the shank; and
 wherein the housing comprises a shank slider operable to be moved along the housing to apply force to the ramp to rotate the shank.

15. The apparatus of claim 14, wherein the housing is formed having a slot and the shank slider having a snap clip which is snap clipped into the slot to mount the shank slider to the housing.

16. The apparatus of claim 14, wherein the housing comprises a foot stop to which the clamping foot is pressable by rotation the shank.

\* \* \* \* \*